United States Patent [19]

Bovy et al.

[11] Patent Number: 5,451,597

[45] Date of Patent: Sep. 19, 1995

[54] TREATMENT OF CIRCULATORY DISORDERS USING N-SUBSTITUTED (α-IMIDAZOLYL-TOLUYL) PYRROLE ANGIOTENSIN II ANTAGONISTS

[75] Inventors: Philippe R. Bovy, St. Louis; Joe T. Collins, Ballwin; Robert E. Manning, St. Louis, all of Mo.

[73] Assignee: G.D. Searle & Co., Chicago, Ill.

[21] Appl. No.: 66,057

[22] Filed: May 27, 1993

[51] Int. Cl.$^6$ .................. A61K 31/415; A61K 31/41; C07D 233/90; C07D 403/04; C07D 403/14

[52] U.S. Cl. ..................... 514/381; 514/383; 514/397; 548/250; 548/251; 548/252; 548/253; 548/254; 548/266.2; 548/266.6; 548/267.8; 548/314.7; 548/312.1

[58] Field of Search ............. 548/314.7, 312.1, 252, 548/253, 251, 250, 254, 266.2, 266.6, 267.8; 514/397, 381, 383

[56] References Cited

U.S. PATENT DOCUMENTS

| | | | |
|---|---|---|---|
| 3,138,610 | 6/1964 | Buc et al. | 260/309.6 |
| 4,156,734 | 5/1979 | Stone | 424/273 R |
| 4,301,169 | 11/1981 | Yamanaka et al. | 424/273 R |
| 4,816,463 | 3/1989 | Blankley et al. | 514/293 |
| 4,880,804 | 11/1989 | Carini et al. | 514/234.5 |
| 5,087,634 | 2/1992 | Reitz et al. | 548/252 |
| 5,187,271 | 2/1993 | Bovy et al. | 548/314.7 |
| 5,276,048 | 1/1994 | Hodges et al. | 514/381 |

FOREIGN PATENT DOCUMENTS

| | | | |
|---|---|---|---|
| 253310 | 1/1988 | European Pat. Off. | C07D 548/252 |
| 323841 | 7/1989 | European Pat. Off. | C07D 548/252 |
| 0510398 | 10/1992 | European Pat. Off. | 548/314.7 |

OTHER PUBLICATIONS

P. C. Wong et al, *J. Pharmacol. Exp. ther.*, 247(1), 1–7 (1988).

A. T. Chiu et al, *European J. Pharmacol.*, 157, 13–21 (1988).

A. T. Chiu et al, *J. Pharmacol. Exp. Ther.*, 250(3), 867–874 (1989).

S. Massa et al, *Arch. Pharm.*, 322(6), 369–73 (1989).

Primary Examiner—Floyd D. Higel
Attorney, Agent, or Firm—J. Timothy Keane

[57] ABSTRACT

A class of N-substituted (α-imidazolyltoluyl)pyrrole compounds is described for use in treatment of circulatory disorders. Compounds of particular interest are angiotensin II antagonists of the formula

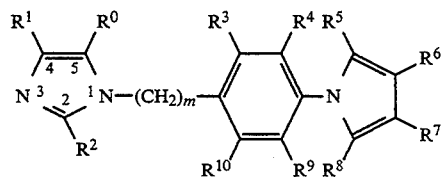

wherein m is one; wherein $R^0$ is selected from $CH_2OH$, $CO_2H$, $CHO$, $CO_2CH_3$, $CO_2C_2H_5$, $CH_2OCH_3$, $CH_2OCHOCH_3$ and $CH_2-CO_2C_2H_5$; wherein $R^1$ is selected from $Cl$, $CF_3$, $CHO$, n-butyl, cyano, $CO_2CH_3$ and $CO_2CH_2CH_3$; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio and hydroxyalkyl; wherein each of $R_3$, $R_4$, $R^6$, $R^7$, $R^9$ and $R^{10}$ is hydrido; wherein each of $R^5$ and $R^8$ is independently selected from hydrido, halo, nitro, trifluoromethyl, hydroxy, alkoxy, cyano, carboxyl, methoxycarbonyl with the proviso that at least one of $R^5$ and $R^8$ is an acidic group selected from $CO_2H$ and tetrazolyl; or a tautomer thereof or a pharmaceutically-acceptable salt thereof. These compounds are particularly useful in treatment or control of hypertension and congestive heart failure.

11 Claims, No Drawings

TREATMENT OF CIRCULATORY DISORDERS USING N-SUBSTITUTED (α-IMIDAZOLYL-TOLUYL) PYRROLE ANGIOTENSIN II ANTAGONISTS

This application is a 371 of US92/01244 filed Feb. 19, 1992.

FIELD OF THE INVENTION

Non-peptidic N-substituted (α-imidazolyltolyl)pyrrol compounds are described for use in treatment of circulatory disorders such as hypertension and congestive heart failure. Of particular interest are angiotensin II antagonist compounds having an N-toluylpyrrole moiety attached to a nitrogen atom of 1H-imidazole.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, the primary active species of this system. This octapeptide, angiotensin II, is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al., J. Pharmacol. Exp. Ther., 247(1), 1–7 (1988). Also, the sodium salt of 2-butyl-4-chloro-1-[2-nitrobenzyl)imidazole-5-acetic acid has specific competitive angiotensin II antagonist activity as shown in a series of binding experiments, functional assays and in vivo tests [A. T. Chiu et al., European J. Pharmacol., 157, 13–21 (1988). A family of 1-benzyl-5-acetate derivatives has been shown to have competitive angiotensin II antagonist properties [A. T. Chiu et al., J. Pharmacol, Exp. Ther., 250(3), 867–874 (1989)]. U.S. Pat. No. 4,816,463 to Blankey et al describes a family of 4,5,6,7-tetrahydro-1H-imidazo(4,5-c)-tetrahydro-pyridine derivatives useful as antihypertensives, some of which are reported to antagonize the binding of labelled angiotensin II to rat adrenal receptor preparation and thus case a significant decrease in mean arterial blood pressure in conscious hypertensive rats. EP No. 253,310, published 20 Jan. 1988, describes a series of aralkyl imidazole compounds, including in particular a family of biphenylmethyl substituted imidazoles, as antagonists to the angiotensin II receptor. EP No. 323,841 published 12 Jul. 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al. describes a family of biphenylmethylbenzimidazole compounds as angiotensin II receptor blockers for use in treatment of hypertension and congestive heart failure.

There are pyrrol-containing compounds known for pharmacalogical purposes. For example, U.S. Pat. No. 4,156,734 describes N-toluyl-substituted pyrrole-2-carboxylic acid compounds for use as antihypertensive agents. A family of 1-[p-methyl-α-[4-(1H-pyrrol-1-yl)phenyl]benzyl] azole compounds is described having antibacterial and antifungal properties, including the specific compound 1-[(4-chlorophenyl)[4-(1H-pyrrol-1-yl)phenyl]methyl]-1H-imidazole [S. Massa et al., Arch. Pharm., 322(6), 369–73 (1989)].

DESCRIPTION OF THE INVENTION

A class of N-substituted (α-imidazolyltolyl)pyrrole compounds is described for use in treating circulatory disorders particularly cardiovascular. This class of compounds, more specifically characterized as N-[(4-alkyl-phenyl)pyrrolyl]-1H-imidazole compounds, is defined by Formula I:

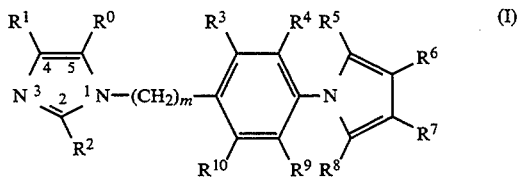

wherein m is a number selected from one to four, inclusive;

wherein each of $R^0$ through $R^{10}$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cyclohetero-containing groups has one or more ring atoms selected from oxygen, sulfur and nitrogen atoms, and wherein each of $R^0$ through $R^{10}$ may be further independently selected from sulfonyl, sulfonylamido, amino and amido radicals of the formula

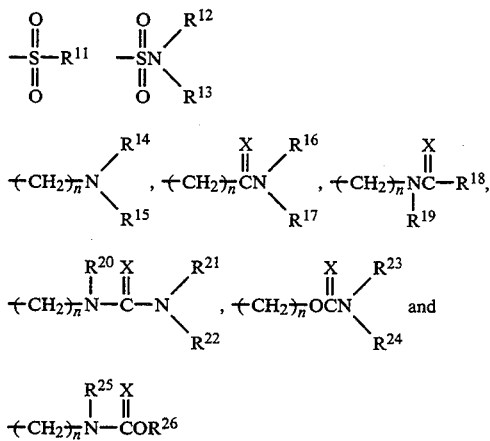

wherein X is oxygen atom or sulfur atom;
wherein each n is a number independently selected from zero to six, inclusive;
wherein each of $R^{11}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{12}$ and $R^{13}$ taken together, and wherein $R^{14}$ and $R^{15}$ taken together, $R^{16}$ and $R^{17}$ taken together, $R^{18}$ and $R^{19}$ taken together, $R^{21}$ and $R^{22}$ taken together and $R^{23}$ and $R^{24}$ taken together may each form a heterocyclic group having five to seven ring members including the hetero atom of said sulfonyl, amino or amido radical and wherein heterocyclic group may further contain one or more hetero atoms as ring members selected from oxygen, nitrogen and sulfur atoms and which heterocyclic group may be saturated or partially unsaturated; wherein $R^{14}$ and $R^{15}$ taken together, $R^{16}$ and $R^{17}$ taken together, $R^{21}$ and $R^{22}$ taken together and $R^{23}$ and $R^{24}$ taken together may each form an aromatic heterocyclic group having five ring members including the nitrogen atom of said amino or amido radical and which aromatic heterocyclic group may further contain one or more additional nitrogen atoms;
and wherein each of $R^3$ through $R^{10}$ may be further independently selected from hydroxy and acidic moieties of the formula $$-Y_nA$$

wherein n is a number selected from zero through three, inclusive, and wherein A is an acidic group selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;
and wherein any of the foregoing $R^0$ through $R^{26}$, Y and A groups having a substitutable position may be substituted by one or more groups independently selected from hydroxy, alkyl, alkenyl, alkynyl, aralkyl, hydroxyalkyl, haloalkyl, halo, oxo, alkoxy, aryloxy, aralkoxy, aralkythio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, aralkoxycarbonyl, carboxyl, mercapto, mercaptocarbonyl, alkylthio, arylthio, alkylthiocarbonyl, alkylsulfinyl, alkylsulfonyl, haloalkylsulfonyl, aralkylsulfinyl, aralkylsulfonyl, arylsulfinyl, arylsulfonyl, heteroaryl, having one or more ring atoms selected from oxygen sulfur and nitrogen atoms,and amino and amido radicals of the formula

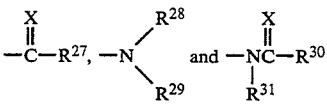

wherein X is oxygen atom or sulfur atom; wherein each of $R^{27}$ through $R^{31}$ is independently selected from hydrido, alkyl, cycloalkyl, cycloalkylalkyl, aralkyl, aryl, $DR^{32}$ and

wherein D is selected from oxygen atom and sulfur atom and $R^{32}$ is selected from hydrido, alkyl, cycloalkyl, cycloalkylalkyl, aralkyl and aryl; wherein each of $R^{27}$, $R^{28}$, $R^{29}$, $R^{39}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{27}$, $R^{28}$, $R^{29}$, $R^{30}$, $R^{31}$, $R^{33}$ and $R^{34}$ is further independently selected from amino and amdio radicals of the formula

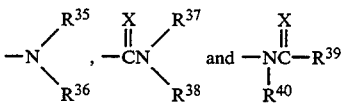

wherein X is oxygen atom or sulfur atom; wherein each of $R^{35}$, $R^{36}$, $R^{37}$, $R^{38}$, $R^{39}$ and $R^{40}$ is independently selected from hydrido, alkyl, cycloalkyl, cyano, hydroxyalkyl, cycloalkylalkyl, alkoxyalkyl, haloalkylsulfinyl, haloalkylsulfonyl, aralkyl and aryl, and wherein each of $R^{28}$ and $R^{29}$ taken together and each of $R^{30}$ and $R^{31}$ taken together may form a heterocyclic group having five to seven ring members including the nitrogen atom of said amino or amido radical, which heterocyclic group may further contain one or more hetero atoms as ring members selected from oxygen, nitrogen and sulfur atoms and which heterocyclic group may be saturated or partially unsaturated; wherein each of $R^{28}$ and $R^{29}$ taken together and each of $R^{33}$ and $R^{34}$ taken together may form an aromatic heterocyclic group having five ring members including the nitrogen atom of said amino or amido radical and which aromatic heterocyclic group may further contain one or more additional nitrogen atoms; or a tautomer thereof or a pharmaceutically-acceptable salt thereof.

Compounds of Formula I would be useful in treating a variety of circulatory disorders; including cardiovascular disorders, such as hypertension, congestive heart failure and arteriosclerosis, and to treat other disorders such as glaucoma. These compounds would also be useful as adjunctive therapies. For example, compounds of Formula I may be used in combination with other drugs, such as a diuretic, to treat hypertension. Also, compounds of Formula I could be used in conjunction with certain surgical procedures. For example, these compounds could be used to prevent post-angioplasty re-stenosis. Compounds of Formula I are therapeutically effective in treatment of cardiovascular disorders by acting as antagonists to, or blockers of, the angiotensin II (AII) receptor. Compounds of Formula I would be therapeutically effective in treatment of the above-mentioned circulatory and cardiovascular disorders or would be precursors to, or prodrugs of, therapeutically-effective compounds.

The phrase "acidic group selected to contain at least one acidic hydrogen atom", as used to define the $-Y_nA$ moiety, is intended to embrace chemical groups which, when attached to any of the $R^3$ through $R^{10}$ positions of Formula I, confers acidic character to the compound of Formula I. "Acidic character" means proton-donor capability, that is, the capacity of the compound of Formula I to be a proton donor in the presence of a proton-receiving substance such as water. Typically, the acidic group should be selected to have proton-donor capability such that the product compound of Formula I has a p$K_a$ in a range from about one to about twelve. More typically, the Formula I compound would have a p$K_a$ in a range from about two to about seven. An example of an acidic group containing at least one acidic hydrogen atom is carboxyl group (—COOH). Where n is zero and A is —COOH, in the $-Y_nA$ moiety, such carboxyl group would be attached directly to one of the $R^3$ through $R^{10}$ positions. The Formula I compound may have one $-Y_nA$ moiety attached at one of the $R^3$ through $R^{10}$ positions, or may have a plurality of such $-Y_nA$ moieties attached at more than one of the $R^3$ through $R^{10}$ positions, up to a maximum of either such $-Y_nA$ moieties. There are many examples of acidic groups, other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisosteres are described hereinafter. Compounds of Formula I having the $-Y_nA$ moiety attached at one of positions $R^5$, $R^6$, $R^7$, and $R^8$ would be expected to have preferred properties, while attachment at $R^5$ or $R^8$ would be more preferred. Compounds of Formula I may have one or more acidic protons and, therefore, may have one or more p$K_a$ values. It is preferred, however, that at least one of these p$k_a$ values of the Formula I compound, as conferred by the $Y_nA$ moiety, be in a range from about two to about seven. The $Y_nA$ moiety may be attached to one of the $R^3$ through $R^{10}$ positions through any portion of the $Y_nA$ moiety which results in a Formula I compound being relatively stable and also having a labile or acidic proton to meet the foregoing p$k_a$ criteria. For example, where the $Y_nA$ acid moiety is tetrazole, the tetrazole could be attached through any ring atom except the tetrazole atom having the acidic hydrogen atom.

A preferred class of compounds consists of those compounds of Formula I wherein m is one; wherein each of $R^0$, $R^1$ and $R^2$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxylalkyl, mercaptoalkyl, alkoxycarbonyloxy, alkylthio, cycloalkylthio, cycloalkylalkylthio, arylthio, arylthiocarbonyl, arylcarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^1$ and $R^2$ through $R^{10}$ may be further independently selected from sulfonyl, sulfonylamido, amino and amido radicals of the formula

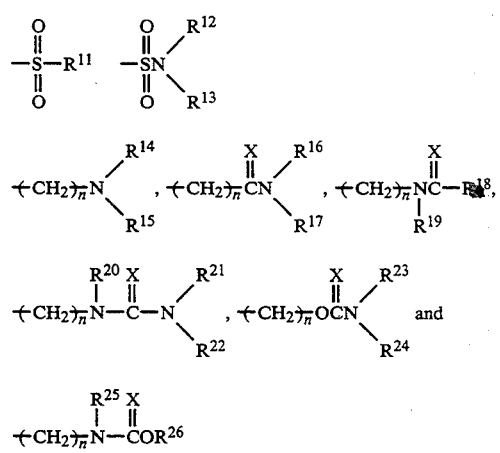

wherein X is selected from oxygen atom or sulfur atom;
wherein each n is a number independently selected from zero to six, inclusive;
wherein each of $R^{11}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^3$ through $R^{10}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercapto, alkylsulfonyl, aralkylsulfonyl and arylsulfonyl, and amino and amido radicals of the formula

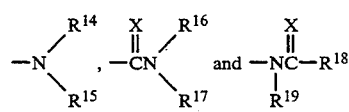

wherein X is oxygen atom or sulfur atom;
wherein each of $R^{14}$, $R^{15}$, $R^{16}$, $R^{17}$, $R^{18}$ and $R^{19}$ is independently selected from hydrido, alkyl, cycloalkyl, cyano, hydroxyalkyl, cycloalkylalkyl, alkoxyalkyl, aralkyl and aryl;
and wherein each of $R^3$ through $R^{10}$ may be further independently selected from acidic moieties of the formula $-Y_nA$ wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^0$ through $R^{26}$, Y and A groups having a substitutable position may be substituted by one or more groups independently selected from hydroxy, alkyl, alkenyl, aralkyl, hydroxyalkyl, halo, haloalkyl, oxo, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

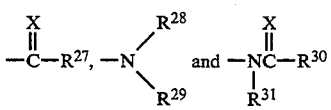

wherein X is oxygen atom or sulfur atom; wherein each of $R^{27}$ through $R^{31}$ is independently selected from hydrido, alkyl, cycloalkyl, cycloalkylalkyl, aralkyl, aryl, and $DR^{32}$ and

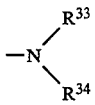

wherein D is selected from oxygen atom and sulfur atom, and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

or a tautomer thereof or a pharmaceutically-acceptable salt thereof.

A more preferred class of compounds consists of those compounds of Formula I wherein m is one; wherein each of $R^0$, $R^1$ and $R^2$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, mercaptocarbonyl, alkoxycarbonyloxy, alkylcarbonyloxyalkyl, alkoxycarbonylalkyl, aralkoxycarbonylalkyl, aralkylcarbonyloxyalkyl, alkylthio, cycloalkylthio, cycloalkylalkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl, wherein each of said heteroaryl- and cycloheteroalkyl- containing groups has one or more hetero ring atoms selected from oxygen, sulfur and nitrogen atoms, and wherein each of $R^0$, $R^1$ and $R^2$ may be further independently selected from sulfonyl, sulfonylamido, amino and amido radicals of the formula

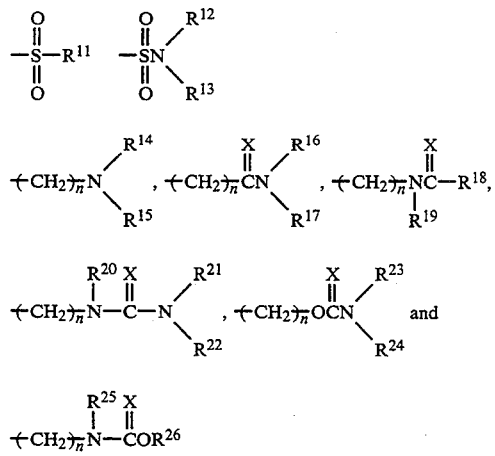

wherein X is selected from oxygen atom or sulfur atom; wherein each n is a number independently selected from zero to six, inclusive;

wherein each of $R^{11}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{10}$ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, arylthio, aralkylthio, mercapto, alkylsulfonyl, aralkylsulfonyl and arylsulfonyl, and amino and amido radicals of the formula

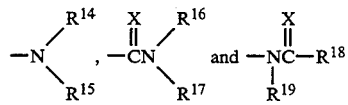

wherein each of $R^{14}$, $R^{15}$, $R^{16}$, $R^{17}$, $R^{18}$ and $R^{19}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{10}$ may be further independently selected from acidic moieties of the formula $-Y_nA$ wherein n is a number selected from zero through three, inclusive;

wherein the A group is selected to have an acidic proton, such that the A moiety when incorporated within a compound of Formula I, results in such compound having a $pk_a$ in a range from about seven, said group from carboxylic acid and bioisosteres of carboxylic acid selected from

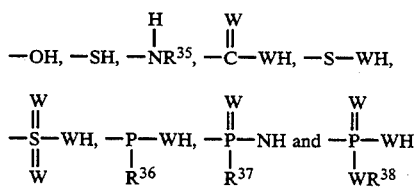

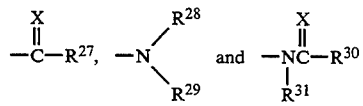

wherein each W is independently selected from oxygen atom, sulfur atom and $NR^{39}$; wherein each of $R^{35}$, $R^{36}$, $R^{37}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$, $R^{36}$, $R^{37}$ and $R^{39}$ may be further independently selected from amino radical of the formula

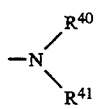

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein $R^{40}$ and $R^{41}$ taken together may form a heterocyclic group having five to seven ring members including the nitrogen atom of said amino radical, wherein heterocyclic group may further contain one or more hetero atoms as ring members selected from oxygen, nitrogen and sulfur atoms and which heterocyclic group may be saturated or partially unsaturated; wherein $R^{40}$ and $R^{41}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; wherein each of $R^{36}$ and $R^{37}$ may be further independently selected from hydroxy, alkoxy, alkylthio, aryloxy, arylthio, aralkylthio and aralkoxy; and the amide, ester and salt derivatives of said acidic groups;

wherein said bioisostere of carboxylic acid may be further selected from heterocyclic acidic groups consisting of heterocyclic rings of four to about nine ring members, which heterocyclic ring contains at least one hetero atom selected from oxygen, sulfur and nitrogen atoms, which heterocyclic ring may be saturated, fully unsaturated or partially unsaturated, and which heterocyclic ring may be attached at a single position selected from $R^3$ through $R^{10}$; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

and wherein any of the foregoing $R^1$ through $R^{26}$ and $R^{35}$ through $R^{41}$, Y and A groups having a substitutable position may be substituted by one or more groups independently selected from hydroxy, alkyl, alkenyl, aralkyl, hydroxyalkyl, halo, oxo, haloalkyl, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula wherein X is selected from oxygen atom and sulfur atom; wherein $R^{27}$ is selected from hydrido, alkyl, cycloalkyl, cycloalkylalkyl, aralkyl, aryl and $DR^{32}$ and

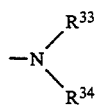

wherein D is selected from oxygen atom and sulfur atom; wherein $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

or a tautomer thereof or a pharmaceutically-acceptable salt thereof.

An even more preferred class of compounds consists of those compounds of Formula I wherein m is one; wherein each of $R^0$, $R^1$ and $R^2$ is independently selected from hydrido, alkyl, hydroxyalkyl, formyl, halo, haloalkyl, cycloalkyl; cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl,alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, arylthio, aralkylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{10}$ may be further independently selected from sulfonyl, sulfonylamido, amino and amido radicals of the formula

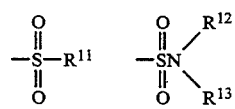

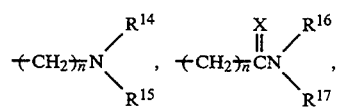

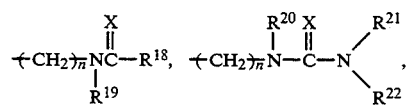

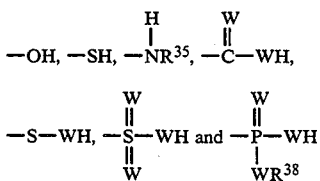

wherein X is selected from oxygen atom and sulfur atom;
wherein each n is a number independently selected from zero to six, inclusive;
wherein each of $R^{11}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^3$ through $R^{10}$ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylthio, aralkylthio and mercapto;
and wherein each of $R^3$ through $R^{10}$ may be further independently selected from acidic moieties of the formula $$-Y_nA$$

wherein n is a number selected from zero through three, inclusive; wherein A is selected from carboxylic acid and bioisosteres of carboxylic acid selected from $$-OH, -SH, -\overset{H}{\underset{|}{N}}R^{35}, -\overset{W}{\underset{\|}{C}}-WH,$$

$$-S-WH, -\overset{W}{\underset{\underset{W}{\|}}{S}}-WH \text{ and } -\overset{W}{\underset{\underset{WR^{38}}{|}}{P}}-WH$$

wherein each W is independently selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$ and $R^{39}$ may be further independently selected from amino radical of the formula

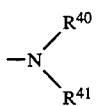

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein $R^{40}$ and $R^{41}$ taken together may form a heterocyclic group having five to seven ring members including the nitrogen atom of said amino radical, which heterocyclic group may further contain one or more hetero atoms as ring members selected from oxygen, nitrogen and sulfur atoms, and which heterocyclic group may be saturated or partially unsaturated; wherein $R^{40}$ and $R^{41}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; and the amide, ester and salt derivatives of said acidic groups; wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{10}$ and the amide, ester and salt derivatives of said heterocyclic acidic groups;
wherein Y is a spacer group independently selected from one or more of alkyl, cycloalkyl, cycloalkylalkyl, alkenyl, aryl and aralkyl;
wherein each of $R^0$ through $R^{26}$, $R^{35}$ and $R^{38}$ through $R^{39}$, Y and A independently may be substituted at any substitutable position with one or more groups selected from alkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;
or a tautomer thereof or a pharmaceutically-acceptable salt thereof.

A highly preferred class of compounds within Formula I consists of those compounds wherein m is one; wherein each of $R^0$, $R^1$ and $R^2$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, alkylcarbonyl, alkoxycarbonyl, alkenyl, cycloalkenyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{10}$ may be further independently selected from sulfonyl, sulfonylamido, amino and amido radicals of the formula

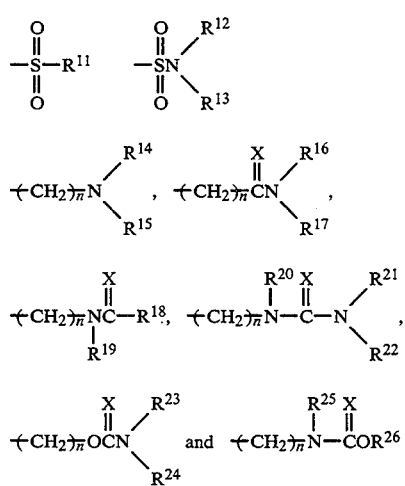

wherein X is selected from oxygen atom and sulfur atom;
wherein each n is a number independently selected from zero to six, inclusive;

wherein each of $R^{11}$ through $R^{26}$ is independently selected from hydrido, alkyl, cycloalkyl, cyano, amino, hydroxyalkyl, alkoxyalkyl, phenalkyl and phenyl;

wherein each of $R^3$ through $R^{10}$ is independently selected from hydrido, hydroxy, alkyl, hydroxyalkyl, halo, haloalkyl, cycloalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio and mercapto;

and wherein each of $R^3$ through $R^{10}$ may be further independently selected from acidic moieties of the formula —$Y_nA$ wherein n is a number selected from zero through two, inclusive; wherein A is selected from carboxylic acid and bioisosteres of carboxylic acid selected from

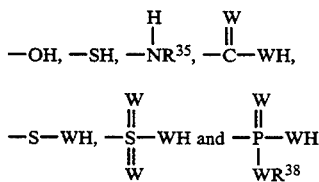

wherein each W is independently selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, phenyl and benzyl; wherein each of $R^{35}$ and $R^{39}$ may be further independently selected from amino radical of the formula

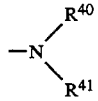

wherein each of $R^{40}$ and $R^{41}$ is independently selected from hydrido, alkyl, cycloalkyl, hydroxyalkyl, haloalkyl, alkoxyalkyl, benzyl and phenyl; and the amide, ester and salt derivatives of said acidic groups;

wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{10}$, and the amide, ester and salt derivatives of said heterocyclic acidic groups;

wherein Y is a spacer group independently selected from one or more of alkyl, cycloalkyl, cycloalkylalkyl, alkenyl, phenyl, phenalkyl and aralkyl;

wherein each of $R^0$, $R^1$ through $R^{26}$, $R^{35}$ and $R^{38}$ through $R^{41}$, Y and A and independently may be substituted at any substitutable position with one or more groups selected from alkyl, cycloalkyl, cycloalkylalkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

An even more highly preferred class of compounds consists of those compounds of Formula I wherein m is one;

where each of $R^0$, $R^1$ and $R^2$ is independently selected from hydrido, alkyl, aminoalkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, carboxyalkyl, alkylcarbonyl, alkycarbonyloxy, mercaptoalkyl, mercaptocarbonyl, alkoxycarbonyloxy, alkylcarbonyloxyalkyl, alkoxycarbonylalkyl, aralkoxycarbonylalkyl, aralkylcarbonyloxyalkyl, phthalimido, phthalimidoalkyl, imidazoalkyl, tetrazole, tetrazolealkyl, alkylthio, cycloalkylthio, cycloalkylalkylthio, and sulfonyl, sulfonylamido, amino and amido radicals of the formula

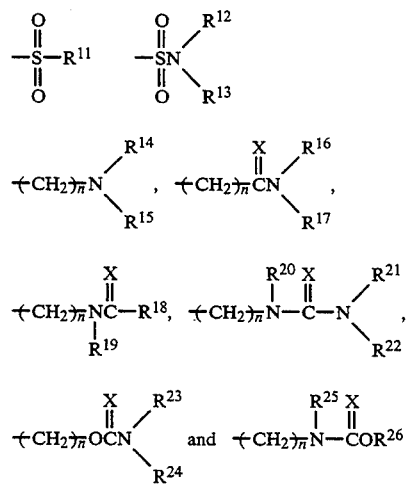

wherein X is selected from oxygen atom and sulfur atom;

wherein each n is a number independently selected from zero to six, inclusive;

wherein each of $R^{11}$ through $R^{26}$ is independently selected from hydrido, alkyl, cycloalkyl, cyano, amino, hydroxyalkyl, alkoxyalkyl, phenalkyl and phenyl;

wherein each of $R^3$ through $R^{10}$ is independently selected from hydrido, hydroxy, alkyl, hydroxyalkyl, halo, haloalkyl, alkoxy, phenyl, benzoyl, phenoxy, alkoxyalkyl, acetyl, alkoxycarbonyl, alkenyl, cyano, nitro carboxyl, alkylthio and mercapto;

and wherein each of $R^3$ through $R^{10}$ may be further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$, $CONHOC_2H_5$, $CONHCF_3$, OH, $CH_2OH$, $C_2H_4OH$, $OPO_3H_2$, $OSO_3H$,

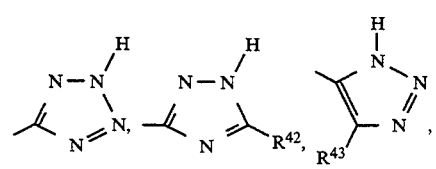

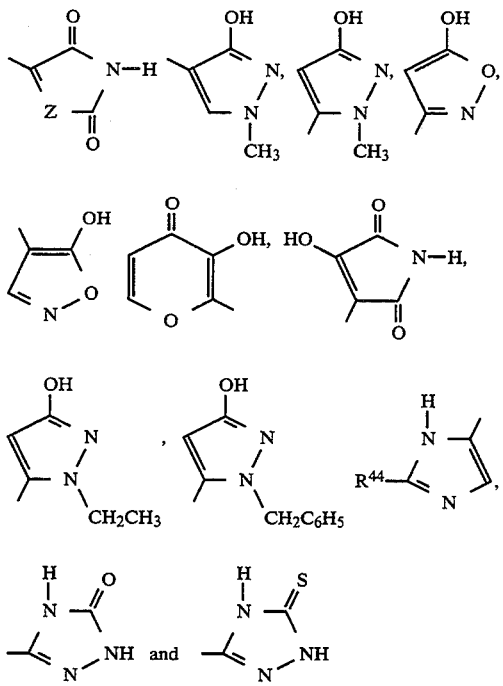

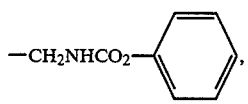

—CH$_2$NHCO$_2$CH$_3$, —CH$_2$NHCO$_2$C$_3$H$_7$, —CH$_2$NHCO$_2$CH$_2$(CH$_3$)$_2$, —CH$_2$NHCO$_2$C$_4$H$_9$, CH$_2$NHCO$_2$-adamantyl, —CH$_2$NHCO$_2$-(1-napthyl), —CH$_2$NHCONHCH$_3$, —CH$_2$NHCONHC$_2$H$_5$, —CH$_2$NHCONHC$_3$H$_7$, —CH$_2$NHCONHC$_4$H$_9$, —CH$_2$NHCONHCH(CH$_3$)$_2$, —CH$_2$NHCONH(1-napthyl), —CH$_2$NHCONH(1-adamantyl),

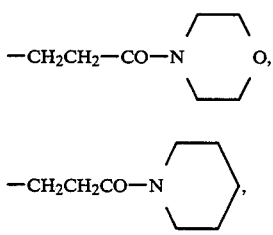

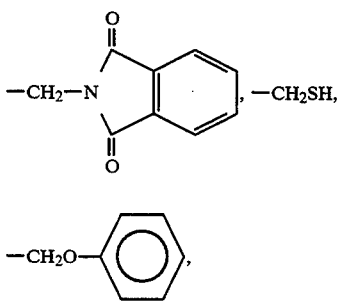

—CH$_2$CH$_2$CH$_2$CO$_2$H, —CH$_2$CH$_2$F, CH$_2$OCONHCH$_3$, —CH$_2$OCSNHCH$_3$, —CH$_2$NHCSOC$_3$H$_7$, —CH$_2$CH$_2$CH$_2$F, —CH$_2$OHO$_2$,

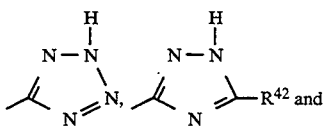

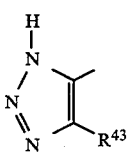

wherein each of R$^{42}$, R$^{43}$ and R$^{44}$ is independently selected from H, Cl, CN, NO$_2$, CF$_3$, C$_2$F$_2$, C$_3$F$_7$, CHF$_2$, CH$_2$F, CO$_2$CH$_3$, CO$_2$C$_2$H$_5$, SO$_2$CH$_3$, SO$_2$CF$_3$ and SO$_2$C$_6$F$_3$; wherein Z is selected from O, S, NR$^{45}$ and CH$_2$; wherein R$^{45}$ is selected from hydrido, CH$_3$ and CH$_2$C$_6$H$_5$; or a tautomer thereof or a pharmaceutically-acceptable salt thereof.

A class of compounds of particular interest consists of those compounds of Formula I wherein m is one; wherein each of R$^0$ and R$^1$ is independently selected from methyl, ethyl, n-proyl, isopropyl, n-butyl, sec-butyl, isobutyl, tert-butyl, n-pentyl, isopentyl, neopentyl, phenyl, benzyl, cyclohexyl, cyclohexylmethyl, cyclohexylethyl, n-hexyl, cyclohexanoyl, 1-oxo-2-cyclohexylethyl, benzoyl, 1-oxo-2-phenethyl, 1-oxoethyl, 1-oxopropyl, 1-oxobutyl, 1-oxopentyl, 2-butenyl, 3-butenyl, 2-butynyl, 3-butynyl and 2-hydroxybutyl selected from CH$_3$CH$_2$CH=CH, SC$_3$H$_7$, SC$_4$H$_9$,

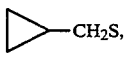

amino, aminomethyl, aminoethyl, aminoproyl, CH$_2$OH, CH$_2$OCHOCH$_3$, CH$_2$Cl, CH$_2$OCH$_3$, CH$_2$OCH(CH$_3$)$_2$, CHO, CH$_2$CO$_2$H, CH(CH$_3$)CO$_2$H, NO$_2$,

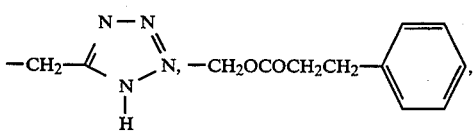

—CONH$_2$, —CONHCH$_3$, CON(CH$_3$)$_2$, —CH$_2$—NHCO$_2$C$_2$H$_5$,

CF$_3$, CH$_2$OH, Br, Cl, F, I, dimethyoxyethyl, 1,1-dimethoxypropyl, 1,1-dimethoxypentyl, hydroxyalkyl, 1-oxo-2-phenylethyl, 1-oxo-2-cyclohexylethyl, 1,1-difluoro-2-phenylethyl, monoflouromethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, 2-phenylethyl, 1,1-difluoro-3-phenylpropyl, difluoromethyl, CO$_2$H, CO$_2$CH$_3$, CO$_2$CH$_2$CH$_3$, SH, PO$_3$H$_2$, SO$_3$H, CONHNH$_2$, CONHNHSO$_2$CF$_3$, OH, wherein each of R$^{42}$ and R$^{43}$ is independently selected from chloro, cyano, nitro, trifluoromethyl, methoxycarbonyl and trifluoromethylsulfonyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of $R^3$ through $R^{10}$ is independently selected from hydrido, halo, nitro, trifluoromethyl, hydroxy, alkoxy, cyano, carboxyl, methoxycarbonyl with the proviso that at least one of $R^4$, $R^6$, $R^7$ and $R^8$ is an acidic group selected from $CO_2H$, SH, $PO_3H_2$, $SO_3H$, $CONHNH_2$, $CONHNHSO_2CF_3$, OH,

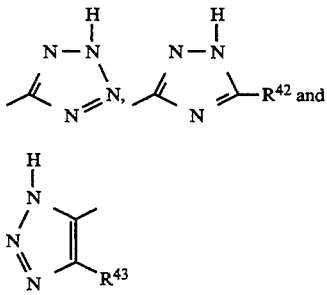

wherein each of $R^{42}$ and $R^{43}$ is independently selected from chloro, cyano, nitro, trifluoromethyl, methoxycarbonyl and trifluoromethylsulfonyl; or a tautomer thereof or a pharmaceutically-acceptable salt thereof.

A class of compounds of more particular interest consists of those compounds of Formula I wherein m is one; wherein $R^0$ is selected from oxoethyl, 1-oxopropyl, 1-oxobutyl, 1-oxopentyl, 2-butenyl, 3-butenyl, 2-butynyl, 3-butynyl and 2-hydroxybutyl selected from $CH_3CH_2CH=CH$, $SC_3H_7$, $SC_4H_9$,

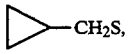

amino, amino, aminomethyl, aminoethyl, aminopropyl, $CH_2OH$, $CH_2OCOCH_3$, $CH_2Cl$, $CH_2I$, $OCH_3$, $CH_2OCH(CH_3)_2$, CHO, $CH_2CO_2H$, $CH(CH_3)CO_2H$, $NO_2$,

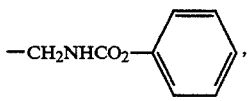

—$CO_2CH_3$, —$CONH_2$, —$CONHCH_3$, $CON(CH_3)_2$, —$CH_2$—$NHCO_2C_2H_5$,

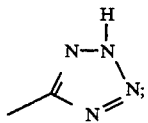

—$CH_2NHCO_2CH_3$, —$CH_2NHCO_2C_3H_7$, —$CH_2NHCO_2CH_2(CH_3)_2$, —$CH_2NHCO_2C_4H_9$, $CH_2NHCO_2$-adamanthyl, —$CH_2NHCO_2$-(1-napthyl), —$CH_2NH$-CONHCH$_3$, —$CH_2NHCONHC_2H_5$, —$CH_2NH$-CONHC$_3H_7$, —$CH_2NHCONHC_4H_9$, —$CH_2NH$-CONHCH(CH$_3$)$_2$, —$CH_2NHCONH$(1-napthyl), —$CH_2NHCONH$(1-adamantyl),

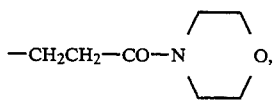

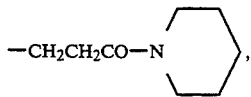

—$CH_2CH_2CH_2CO_2H$, —$CH_2CH_2F$, —$CH_2OCONHCH_3$, —$CH_2OCSNHCH_3$, —$CH_2NHCSOC_3H_7$, —$CH_2CH_2CH_2F$, —$CH_2ONO_2$,

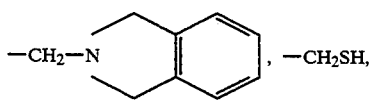

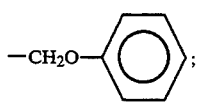

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, $CF_3$, $CH_2OH$, Br, Cl, F, I, dimethoxymethyl, 1,1-dimethoxypropyl, 1,1-dimethoxypentyl, 1,1-dimethoxypentyl, hydroxyalkyl, 1-oxo-2-phenylethyl, 1-oxo-2-cyclohexylethyl, 1,1-difluoro-2-phenylethyl, phenylethyl, monofluoromethyl, 1,1-difluoro-2-cyclohexylethyl, 2-cyclohexylethyl, 1,1-difluoro-2-cyclohexylpropyl, 1,1-dimethoxybutyl, 1,1-difluoroethyl, 1,1-difluoropropyl, 1,1-difluorobutyl, 1,1-difluoropentyl, 2-phenylethyl, 1,1-difluoro-3-phenylpropyl, difluoromethyl, $CO_2H$, $CO_2CH_3$, $CO_2CH_2CH_3$, SH, $PO_3H_2$, $SO_3H$, $CONHNH_2$, $CONHNHSO_2CF_3$ and OH; wherein each of $R^3$, $R^4$, $R^6$, $R^7$, $R^9$ and $R^{10}$ is hydrido; wherein each of $R^5$, $R^6$, $R^7$ and $R^8$ is independently selected from hydrido, halo, nitro, trifluoromethyl, hydroxy, alkoxy, cyano, carboxyl, methoxycarbonyl with the proviso that at least one of $R^5$ and $R^8$ is an acidic group selected from $CO_2H$ and

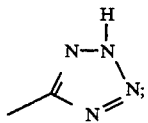

or a tautomer thereof or a pharmaceutically-acceptable salt thereof.

A class of compounds of even more particular interest consists of those compounds of Formula I wherein m is one; wherein $R^0$ is selected from $CH_2OH$, $CO_2H$, CHO, $CO_2CH_3$, $CO_2C_2H_5$, $CH_2OCH_3$, $CH_2O$-CHOCH$_3$ and $CH_2$—$CO_2C_2H_5$; wherein $R^1$ is selected from Cl, $CF_3$, CHO, n-butyl, cyano, $CO_2CH_3$ and $CO_2CH_2CH_3$; wherein $R^2$ is selected from ethyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio and hydroxyalkyl; wherein each of $R^3$, $R^4$, $R^6$, $R^7$, $R^9$ and $R^{10}$ is hydrido; wherein each of $R^5$, $R^6$, $R^7$ and $R^8$ is independently selected from hydrido, halo, nitro, trifluoromethyl, hydroxy, alkoxy, cyano, carboxyl, methoxycarbonyl with the proviso that at least one of $R^5$ and $R^8$ is an acidic group selected from $CO_2H$ and

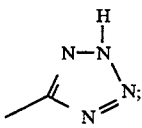

or a tautomer thereof or a pharmaceutically-acceptable salt thereof.

The term "hydrido" denotes a single hydrogen atom (H). This hydrido group may be attached, for example, to an oxygen atom to form a hydroxyl group; or, as another example, one hydrido group may be attached to a carbon atom to form a

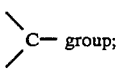

or, as another example, two hydrido groups may be attached to a carbon atom to form a —$CH_2$— group, Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "aryl" embraces aromatic radicals such as phenyl, napthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment. For any of the foregoing defined radicals, preferred radicals are those containing from one to about ten carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Compounds of Formula I have been found to inhibit the action of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from or afflicted by the effects of hypertension or susceptible to a hypertensive condition if not treated to prevent or control such hypertension.

Also included in the family of compounds of Formula I are isomeric forms including diastereoisomers, regioisomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

A family of specific compounds of interest within Formula consists of compounds and pharmaceutically-acceptable salts thereof, as follows:

1-[4-[(2-butyl-4-chloro-5-hydroxymethyl-1H-imidazol-1-yl)methyl]phenyl]-1H-pyrrole-2-carbonitrile;

1-[4-[(2-butyl-4-chloro-5-hydroxymethyl-1H-imidazol-1-yl)methyl]phenyl]-1H-pyrrole-2-carboxylic acid, methyl ester;

1-[4-[(2-butyl-4-chloro-5-hydroxymethyl-1H-imidazol-1-yl)methyl]phenyl]-1H-pyrrole-2-carboxylic acid;

5-[1-[4-[(2-butyl-4-chloro-5-hydroxymethyl-1H-imidazol-1-yl)methyl]phenyl]-1H-pyrrol-2-yl]-1H-tetrazole;

5-[1-[4-[(2-butyl-5-chloro-4-hydroxymethyl-1H-imidazol-1-yl)methyl]phenyl]methyl]-1H-pyrrol-2-yl]-1H-tetrazole;

5-[1-[4-[(2-butyl-5-chloro-4-hydroxymethyl-1H-imidazol-1-yl)methyl]phenyl]-3,5-dichloro-1H-pyrrol-2-yl]-1H-tetrazole;

5-[1-[4-[(2-butyl-5-chloro-4-hydroxymethyl-1H-imidazol-1-yl)methyl]phenyl]-3,5-dichloro-1H-pyrrol-2-yl]-1H-tetrazole;

5-[1-[4-[(2-butyl-5-chloro-4-hydroxymethyl-1H-imidazol-1-yl)methyl]phenyl]-5-bromo-1H-pyrrol-3-yl]-1H-tetrazole;

5-[1-[4-[(2-butyl-5-chloro-4-hydroxymethyl-1H-imidazol-1-yl)methyl]phenyl]-5-trifluoromethyl-1H-pyrrol-2-yl]-1H-tetrazole;

5-[1-[4-[(2-butyl-5-chloro-4-hydroxymethyl-1H-imidazol-1-yl)methyl]phenyl]-5-chloro-1H-pyrrol-2-yl]-1H-tetrazole;

5-[1-[4-[(2-butyl-5-chloro-4-hydroxymethyl-1H-imidazol-1-yl)methyl]phenyl]-3-bromo-1H-pyrrol-2-yl]-1H-tetrazole;

5-[1-[4-[(2-butyl-5-chloro-4-hydroxymethyl-1H-imidazol-1-yl)methyl]phenyl]-3,5-dibromo-1H-pyrrol-2-yl]-1H-tetrazole;

5-[1-[4-[(2-butyl-5-chloro-4-hydroxymethyl-1H-imidazol-1-yl)methyl]phenyl]-5-bromo-1H-pyrrol-2-yl]-1H-tetrazole;

1-[4-[(2-butyl-4-hydroxymethyl-5-chloro-1H-imidazol-1-yl)methyl]phenyl]-1H-pyrrol-2-yl-carbonitrile;

1-[4-[(2-butyl-4-hydroxymethyl-5-chloro-1H-imidazol-1-yl)methyl]phenyl]-1H-pyrrol-2-yl-carboxylic acid, methyl ester;

1-[4-[(2-butyl-4-hydroxymethyl-5-chloro-1H-imidazol-1-yl)methyl]phenyl]-1H-pyrrol-2-yl-carboxylic acid;

5-[1-[4-[(2-butyl-4-hydroxymethyl-5-chloro-1H-imidazol-1-yl)methyl]phenyl]-1H-pyrrol-2-yl]-1H-tetrazole;

5-[1-[4-[(2-butyl-4-hydroxymethyl-5-chloro-1H-imidazol-1-yl)methyl]phenyl]methyl]-1H-pyrrol-2-yl]-1H-tetrazole;

5-[1-[4-[(2-butyl-4-hydroxymethyl-5-chloro-1H-imidazol-1-yl)methyl]phenyl]-3,5-dichloro-1H-pyrrol-2-yl]-1H-tetrazole;

5-[1-[4-[(2-butyl-4-hydroxymethyl-5-chloro-1H-imidazol-1-yl)methyl]phenyl]-1H-pyrrol-3-yl]-1H-tetrazole;

5-[1-[4-[(2-butyl-4-hydroxymethyl-5-chloro-1H-imidazol-1-yl)methyl]phenyl]-5-bromo-1H-pyrrol-2-yl]-1H-tetrazole;

5-[1-[4-[(2-butyl-4-hydroxymethyl-5-chloro-1H-imidazol-1-yl)methyl]phenyl]-5-trifluoromethyl-1H-pyrrol-2-yl]-1H-tetrazole;

5-[1-[4-[(2-butyl-4-hydroxymethyl-5-chloro-1H-imidazol-1-yl)methyl]phenyl]-5-chloro-1H-pyrrol-2-yl]-1H-tetrazole;

5-[1-[4-[(2-butyl-4-hydroxymethyl-5-chloro-1H-imidazol-1-yl)methyl]phenyl]-3-bromo-1H-pyrrol-2-yl]-1H-tetrazole;

5-[1-[4-[(2-butyl-4-hydroxymethyl-5-chloro-1H-imidazol-1-yl)methyl]phenyl]-3,5-dibromo-1H-pyrrol-2-yl]-1H-tetrazole;

5-[1-[4-[(2-butyl-4-hydroxymethyl-5-chloro-1H-imidazol-1-yl)methyl]phenyl]-5-bromo-1H-pyrrol-2-yl]-1H-tetrazole;

1-[4-[(2-butyl-4,5-dichloro-1H-imidazol-1-yl)methyl]phenyl]-1H-pyrrole-2-carbonitrile;

1-[4-[(2-butyl-4,5-dichloro-1H-imidazol-1-yl)methyl]phenyl]-1H-pyrrole-2-carboxylic acid, methyl ester;

1-[4-[(2-butyl-4,5-dichloro-1H-imidazol-1-yl)methyl]phenyl]-1H-pyrrole-2-carboxylic acid;

5-[1-[4-[(2-butyl-4,5-dichloro-1H-imidazol-1-yl)methyl]phenyl]-1H-pyrrol-2-yl]-1H-tetrazole;

5-[1-[4-[(2-butyl-4,5-dichloro-1H-imidazol-1-yl)methyl]phenyl]methyl]-1H-pyrrol-2-yl]-1H-tetrazole;

5-[1-[4-[(2-butyl-4,5-dichloro-1H-imidazol-1-yl)methyl]phenyl]-3,5-dichloro-1H-pyrrol-2-yl]-1H-tetrazole;

5-[1-[4-[(2-butyl-4,5-dichloro-1H-imidazol-1-yl)methyl]phenyl]-1H-pyrrol-3-yl]-1H-tetrazole;

5-[1-[4-[(2-butyl-4,5-dichloro-1H-imidazol-1-yl)methyl]phenyl]-5-bromo-1H-pyrrol-2-yl]-1H-tetrazole;

5-[1-[4-[(2-butyl-4,5-dichloro-1H-imidazol-1-yl)methyl]phenyl]-5-trifluoromethyl-1H-pyrrol-2-yl]-1H-tetrazole;

5-[1-[4-[(2-butyl-4,5-dichloro-1H-imidazol-1-yl)methyl]phenyl]-5-chloro-1H-pyrrol-2-yl]-1H-tetrazole;

5-[1-[4-[(2-butyl-4,5-dichloro-1H-imidazol-1-yl)methyl]phenyl]-3-bromo-1-H-pyrrol-2-yl]-1H-tetrazole;

5-[1-[4-[(2-butyl-4,5-dichloro-1H-imidazol-1-yl)methyl]phenyl]-5-bromo-1H-pyrrol-2-yl]-1H-tetrazole;

1-[4-[(2-butyl-4-pentafluoroethyl-5-hydroxymethyl-1H-imidazol-1-yl)methyl]phenyl]-1H-pyrrol-2-yl-carbonitrile;

1-[4-[(2-butyl-4-pentafluoroethyl-5-hydroxymethyl-1H-imidazol-1-yl)methyl]phenyl]-1H-pyrrol-2-yl-carboxylic acid, methyl ester;

1-[4-[(2-butyl-4-pentafluoroethyl-5-hydroxymethyl-1H-imidazol-1-yl)methyl]phenyl]-1H-pyrrol-2-yl-carboxylic acid;

5-[1-4-[(2-butyl-4-pentafluoroethyl-5-hydroxymethyl-1H-imidazol-1-yl)methyl]phenyl]-1H-pyrrole-2-yl]-1H-tetrazole;

5-[1-[4-[(2-butyl-4-pentafluoroethyl-5-hydroxymethyl-1H-imidazol-1-yl)methyl]phenyl]methyl]-1H-pyrrol-2-yl]-1H-tetrazole;

5-[1-[4-[(2-butyl-4-pentafluoroethyl-5-hydroxymethyl-1H-imidazol-1-yl)methyl]phenyl]-3,5-dichloro-1H-pyrrol-2-yl]-1H-tetrazole;

5-[1-[4-[(2-butyl-4-pentafluoroethyl-5-hydroxymethyl-1H-imidazol-1-yl)methyl]phenyl]-1H-pyrrol-3-yl]-1H-tetrazole;

5-[1-[4-[(2-butyl-4-pentafluoroethyl-5-hydroxymethyl-1H-imidazol-1-yl)methyl]phenyl]-5-bromo-1H-pyrrol-2-yl)]-1H-tetrazole;

5-(1-[4-[(2-butyl-4-pentafluoroethyl-5-hydroxymethyl-1H-imidazol-1-yl)methyl]phenyl]-5-trifluoromethyl-1H-pyrrol-2-yl]-1H-tetrazole;

5-[1-[4-[(2-butyl-4-pentafluoroethyl-5-hydroxymethyl-1H-imidazol-1-yl)methyl]phenyl]-3-bromo-1H-pyrrol-2-yl]-1H-tetrazole;

5-[1-[4-[(2-butyl-4-pentafluoroethyl-5-hydroxymethyl-1H-imidazol-1-yl)methyl]phenyl]-3-bromo-1H-pyrrol-2-yl]-1H-tetrazole;

5-[1-[4-[(2-butyl-4-pentafluoroethyl-5-hydroxymethyl-1H-imidazol-1-yl)methyl]phenyl]-3,5-dibromo-1H-pyrrol-2-yl]-1H-tetrazole;

5-[1-[4-[(2-butyl-4-pentafluoroethyl-5-hydroxymethyl-1H-imidazol-1-yl)methyl]phenyl]-5-bromo-1H-pyrrol-2-yl]-1H-tetrazole;

1-[4-[(2-butyl-4-chloro-5-methyloxymethyl-1H-imidazol-1-yl)methyl]phenyl]-1H-pyrrole-2-carbonitrile;

1-[4-[(2-butyl-4-chloro-5-methyloxymethyl-1H-imidazol-1-yl)methyl]phenyl]-1H-pyrrole-2-carboxylic acid, methyl ester;

1-[4-[(2-butyl-4-chloro-5-methyl-1H-imidazol-1-yl)methyl]phenyl]-1H-pyrrole-2-carboxylic acid;

5-[1-[4-[(2-butyl-4-chloro-5-methyloxymethyl-1H-imidazol-1-yl)methyl]phenyl]-1H-pyrrol-2-yl]-1H-tetrazole;

5-[1-[4-[(2-butyl-4-chloro-5-methoxymethyl-1H-imidazol-1-yl)methyl]phenyl]methyl]-1H-pyrrol-2-yl]-1H-tetrazole;

5-[1-[4-[(2-butyl-4-chloro-5-methoxymethyl-1H-imidazol-1-yl)methyl]phenyl]-3,5-dichloro-1H-pyrrol-2-yl]-1H-tetrazole;

5-[1-[4-[(2-butyl-4-chloro-5-methoxymethyl-1H-imidazol-1-yl)methyl]phenyl]-1H-pyrrol-3-yl]-1H-tetrazole;

5-[1-[4-[(2-butyl-4-chloro-5-methoxymethyl-1H-imidazol-1-yl)methyl]phenyl]-5-bromo-1H-pyrrol-2-yl]-1H-tetrazole;

5-[1-[4-[(2-butyl-4-chloro-5-methoxymethyl-1H-imidazol-1-yl)methyl]phenyl]-5-trifluoromethyl-1H-pyrrol-2-yl]-1H-tetrazole;

5-[1-[4-[(2-butyl-4-chloro-5-methoxymethyl-1H-imidazol-1-yl(methyl]phenyl]-5-chloro-1H-tetrazole;

5-[1-[4-(2-butyl-4-chloro-5-methoxymethyl-1H-imidazol-1-yl)methyl]phenyl]-3-bromo-1H-pyrrol-2-yl]-1H-tetrazole;

5-[1-[4-[(2-butyl-4-chloro-5-methoxymethyl-1H-imidazol-1-yl)methyl]phenyl]-5-bromo-1H-pyrrol-2-yl]-1H-tetrazole;

1-[4-[(2-butyl-4-chloro-5-methoxycarbonyl-1H-imidazol-1-yl)methyl]phenyl]-1H-pyrrol-2-yl-carbonitrile;

1-[4-8      (2-butyl-4-chloro-5-methoxycarbonyl-1H-imidazol-1-yl)methyl]phenyl]-1H-pyrrol-2-yl-carboxylic acid, methyl ester;

1-[4-[(2-butyl-4-chloro-5-methoxycarbonyl-1H-imidazol-1-yl)methyl]phenyl]-1H-pyrrol-2-yl-carboxylic acid;

5-[1-[4-8      (2-butyl-4-chloro-5-methoxycarbonyl-1H-imidazol-1-yl)methyl]phenyl]-1H-pyrrol-2-yl]-1H-tetrazole;

5-[1-[4-[(2-butyl-4-chloro-5-methoxycarbonyl-1H-imidazol-1-yl)methyl]phenyl]methyl]-1H-pyrrol-2-yl]-1H-tetrazole;

5-[1-[4-[(2-butyl-4-chloro-5-methoxycarbonyl-1H-imidazol-1-yl)methyl]phenyl]-3,5-dichloro-1H-pyrrol-2-yl]-1H-tetrazole;

5-[1-[4-[(2-butyl-4-chloro-5-methoxycarbonyl-1H-imidazol-1-yl)methyl]phenyl]-1H-pyrrol-3-yl]-1H-tetrazole;

5-[1-[4-[(2-butyl-4-chloro-5-methoxycarbonyl-1H-imidazol-1-yl)methyl]phenyl]-5-bromo-1H-pyrrol-2-yl]-1H-tetrazole;

5-[1-[4-[(2-butyl-4-chloro-5-methoxycarbonyl-1H-imidazol-1-yl)methyl]phenyl]-5-trifluoromethyl-1H-pyrrol-2-yl]-1H-tetrazole;

5-[1-[4-[(2-butyl-4-chloro-5-methoxycarbonyl-1H-imidazol-1-yl)methyl]phenyl]-5-chloro-1H-pyrrol-2-yl]-1H-tetrazole;

5-[1-[4-[(2-butyl-4-chloro-5-methoxycarbonyl-1H-imidazol-1-yl)methyl]phenyl]-3-bromo-1H-pyrrol-2-yl]-1H-tetrazole;

5-[1-[4-[(2-butyl-4-chloro-5-methoxycarbonyl-1H-imidazol-1-yl)methyl]phenyl]-3,5-dibromo-1H-pyrrol-2-yl]-1H-tetrazole;

5-[1-[4-[(2-butyl-4-chloro-5-methoxycarbonyl-1H-imidazol-1-yl)methyl]phenyl]-5-bromo-1H-pyrrol-2-yl]-1H-tetrazole;

1-[4-[(2-butyl-4,5-dibromo-1H-imidazol-1-yl)methyl]phenyl]-1H-pyrrole-2-carbonitrile;

1-[4-[(2-butyl-4,5-dibromo-1H-imidazol-1-yl)methyl]phenyl]-1H-pyrrole-2-carboxylic acid, methyl ester;

1-[4-[(2-butyl-4,5-dibromo-1H-imidazol-1-yl)methyl]phenyl]-1H-pyrrole-2-carboxylic acid;

5-[1-[4-[(2-butyl-4,5-dibromo-1H-imidazol-1-yl)methyl]phenyl]-1H-pyrrol-2-yl]-1H-tetrazole;

5-[1-[[4-[(2-butyl-4,5-dibromo-1H-imidazol-1-yl)methyl]phenyl]methyl]-1H-pyrrol-2-yl]-1H-tetrazole;

5-[1-[4-[(2-butyl-4,5-dibromo-1H-imidazol-1-yl)methyl]phenyl]-3,5-dichloro-1H-pyrrol-2-yl]-1H-tetrazole;

5-[1-[4-[(2-butyl-4,5-dibromo-1H-imidazol-1-yl)methyl]phenyl]-1H-pyrrol-3-yl]-1H-tetrazole;

5-[1-[4-[(2-butyl-4,5-dibromo-1H-imidazol-1-yl)methyl]phenyl]-5-bromo-1H-pyrrol-2-yl]-1H-tetrazole;

5-[1-[4-[(2-butyl-4,5-dibromo-1H-imidazol-1-yl)methyl]phenyl]-5-trifluoromethyl-1H-pyrrol-2-yl]-1H-tetrazole;

5-[1-[4-[(2-butyl-4,5-dibromo-1H-imidazol-1-yl)methyl]phenyl]-5-chloro-1H-pyrrol-2-yl]-1H-tetrazole;

5-[1-[4-[(2-butyl-4,5-dibromo-1H-imidazol-1-yl)methyl]phenyl]-3-bromo-1H-pyrrol-2-yl]-1H-tetrazole;

5-[1-[4-[(2-butyl-4,5-dibromo-1H-imidazol-1-yl)methyl]phenyl]-5-bromo-1H-pyrrol-2-yl]-1H-tetrazole;

1-[4-[(2-butyl-4-chloro-5-acetoxymethyl-1H-imidazol-1-yl)methyl]phenyl]-1H-pyrrol-2-yl-carbonitrile;

1-[4-[(2-butyl-4-chloro-5-acetoxymethyl-1H-imidazol-1-yl)methyl]phenyl]-1H-pyrrol-2-yl-carboxylic acid, methyl ester;

1-[4-[(2-butyl-4-chloro-5-acetoxymethyl-1H-imidazol-1-yl)methyl]phenyl]-1H-pyrrol-2-yl-carboxylic acid;

5-[1,4-[(2-butyl-4-chloro-5-acetoxymethyl-1H-imidazol-1-yl)methyl]phenyl]-1H-pyrrol-2-yl]-1H-tetrazole;

5-[1-[4-[(2-butyl-4-chloro-5-acetoxymethyl-1H-imidazol-1-yl)methyl]phenyl]methyl]-1H-pyrrol-2-yl]-1H-tetrazole;

5-[1-[4-[(2-butyl-4-chloro-5-acetoxymethyl-1H-imidazol-1-yl)methyl]phenyl]-3,5-dichloro-1H-pyrrol-2-yl]-1H-tetrazole;

5-[1-[4-[(2-butyl-4-chloro-5-acetoxymethyl-1H-imidazol-1-yl)methyl]phenyl]-1H-pyrrol-3-yl]-1H-tetrazole;

5-[1-[4-[(2-butyl-4-chloro-5-acetoxymethyl-1H-imidazol-1-yl)methyl]phenyl]-5-bromo-1H-pyrrol-2-yl]-1H-tetrazole;

5-[1-[4-[(2-butyl-4-chloro-5-acetoxymethyl-1H-imidazol-1-yl)methyl]phenyl]-5-trifluoromethyl-1H-pyrrol-2-yl]-1H-tetrazole;

5-[1-[4-[(2-butyl-4-chloro-5-acetoxymethyl-1H-imidazol-1-yl)methyl]phenyl]-5-chloro-1H-pyrrol-2-yl]-1H-tetrazole;

5-[1-[4-[(2-butyl-4-chloro-5-acetoxymethyl-1H-imidazol-1-yl)methyl]phenyl]-3-bromo-1H-pyrrol-2-yl]-1H-tetrazole;

5-[1-[4-[(2-butyl-4-chloro-5acetoxymethyl-1H-imidazol-1-yl)methyl]phenyl]-3,5-dibromo-1H-pyrrol-2-yl]-1H-tetrazole; and 5-[1-[4-[(2-butyl-4-chloro-5-acetoxymethyl-1H-imidazol-1-yl)methyl]phenyl]-5-bromo-1H-pyrrol-2-yl]-1H-tetrazole.

A family of specific compounds of more particular interest within Formula I consists of compounds and pharmaceutically-acceptable salts thereof, as follows:

1-[4-[(2-butyl-4-chloro-5-hydroxymethyl-1H-imidazol-1-yl)methyl]phenyl]-1H-pyrrole-2-carbonitrile;

1-[4-[(2-butyl-4-chloro-5-hydroxymethyl-1H-imidazol-1-yl)methyl]phenyl]-1H-pyrrole-2-carboxylic acid, methyl ester;

1-[4-[(2-butyl-4-chloro-5-hydroxymethyl-1H-imidazol-1-yl)methyl]phenyl]-1H-pyrrole-2-carboxylic acid;

5-[1-[4-[(2-butyl-4-chloro-5-hydroxymethyl-1H-imidazol-1-yl)methyl]phenyl]-1H-pyrrol-2-yl]-1H-tetrazole;

1-[4-[(2-butyl-4-hydroxymethyl-5-chloro-1H-imidazol-1-yl)methyl]phenyl]-1H-pyrrol-2-yl-carbonitrile;

1-[4-[(2-butyl-4-hydroxymethyl-5-chloro-1H-imidazol-1-yl)methyl]phenyl]-1H-pyrrol-2-yl-carboxylic acid, methyl ester;

1-[4-[(2-butyl-4-hydroxymethyl-5-chloro-1H-imidazol-1-yl)methyl]phenyl]-1H-pyrrol-2-yl-carboxylic acid;

5-[1-[4-[(2-butyl-4-hydroxymethyl-5-chloro-1H-imidazol-1-yl)methyl]phenyl]-1H-pyrrol-2-yl]-1H-tetrazole;

1-[4-[(2-butyl-4,5-dichloro-1H-imidazol-1-yl)methyl]phenyl]-1H-pyrrole-2-carbonitrile;

1-[4-[(2-butyl-4,5-dichloro-1H-imidazol-1-yl)methyl]phenyl]-1H-pyrrole-2carboxylic acid, methyl ester;

1-[4-[(2-butyl-4,5-dichloro-1H-imidazol-1-yl)methyl]phenyl]-1H-pyrrole-2-carboxylic acid;

5-[1-[4-[(2-butyl-4,5-dichloro-1H-imidazol-1-yl)methyl]phenyl]-1H-pyrrol-2-yl]-1H-tetrazole;

1-[4-[(2-butyl-4-pentafluoroethyl-5-hydroxymethyl-1H-imidazol-1-yl)methyl]phenyl]-1H-pyrrol-2-yl-carbonitrile;

1-[4-[(2-butyl-4-pentafluoroethyl-5-hydroxymethyl-1H-imidazol-1-yl)methyl]phenyl]-1H-pyrrol-2-yl-carboxylic acid, methyl ester;

1-[4-[(2-butyl-4-pentafluoroethyl-5-hydroxymethyl-1H-imidazol-1-yl)methyl]phenyl]-1H-pyrrol-2-yl-carboxylic acid;

5-[1-[(2-butyl-4-pentafluoroethyl-5-hydroxymethyl-1H-imidazol-1-yl)methyl]phenyl]-1H-pyrrol-2-yl]-1H-tetrazole;

1-[4-[(2-butyl-4-chloro-5-methoxymethyl-1H-imidazol-1-yl)methyl]phenyl]-1H-pyrrole-2-carbonitrile;

1-[4-[(2-butyl-4-chloro-5-methoxymethyl-1H-imidazol-1-yl)methyl]phenyl]-1H-pyrrole-2-carboxylic acid, methyl ester;

1-[4-[(2-butyl-4-chloro-5-methoxymethyl-1H-imidazol-1-yl)methyl]phenyl]-1H-pyrrole-2-carboxylic acid;

5-[1-[4-[(2-butyl-4-chloro-5-methoxymethyl-1H-imidazol-1-yl)methyl]phenyl]-1H-pyrrol-2-yl]-1H-tetrazole;

1-[4-[(2-butyl-4-chloro-5-methoxycarbonyl-1H-imidazol-1-yl)methyl]phenyl]-1H-pyrrol-2-yl-carbonitrile;

1-[4-[(2-butyl-4-chloro-5-methoxycarbonyl-1H-imidazol-1-yl)methyl]phenyl]-1H-pyrrol-2-yl-carboxylic acid, methyl ester;

1-[4-[(2-butyl-4-chloro-5-methoxycarbonyl-1H-imidazol-1-yl)methyl]phenyl]-1H-pyrrol-2-yl-carboxylic acid;

5-[1-[4-[(2-butyl-4-chloro-5-methoxycarbonyl-1H-imidazol-1-yl)methyl]phenyl]-1H-pyrrol-2-yl]-1H-tetrazole;

1-[4-[(2-butyl-4,5-dibromo-1H-imidazol-1-yl)methyl]phenyl]-1H-pyrrole-2-carbonitrile;

1-[4-[(2-butyl-4,5-dibromo-1H-imidazol-1-yl)methyl]-
phenyl]-1H-pyrrole-2-carboxylic acid, methyl ester;
1-[4-[(2-butyl-4,5-dibromo-1H-imidazol-1-yl)methyl]-
phenyl]-1H-pyrrole-2-carboxylic acid;
5-[1-[(2-butyl-4,5-dibromo-1H-imidazol-1-yl)methyl]-
phenyl]-1H-pyrrol-2-yl]-1H-tetrazole;
1-[4-[(2-butyl-4-chloro-5-acetoxymethyl-1H-imidazol-
1-yl)methyl]phenyl]-1H-pyrrol-2-yl-carbonitrile;
1-[4-[(2-butyl-4-chloro-5-acetoxymethyl-1H-imidazol-
1-yl)methyl]phenyl]-1H-pyrrol-2-yl-carboxylic acid,
methyl ester;
1-[4-[(2-butyl-4-chloro-5-acetoxymethyl-1H-imidazol-
1-yl)methyl]phenyl]-1H-pyrrol-2-yl-carboxylic acid;
and
5-[1-[4-[(2-butyl-4-chloro-5-acetoxymethyl-1H-
imidazol-1-yl)methyl]phenyl]-1H-pyrrol-2-yl]-1H-
tetrazole.

GENERAL SYNTHETIC PROCEDURES the compounds of the invention can be synthesized in accordance to the following procedures which are modeled upon a subset of biphenylmethyl carboxylic acid or biphenylmethyl tetrazole compounds of the family of compounds of Formula I. The reactions are performed in a solvent appropriate to the reagent and material employed and suitable to the transformation being performed. Some of the steps will involve reagents and substrates with functionality that will require protection. For the synthetic description and examples which follow, abbreviations which have been used have the following meanings:

CHCl$_3$ = chloroform
DMF = dimethylformamide
DMSO = dimethylsulfoxide
g = gram
Me = methyl
MeOH = methanol
min = minute
h = hour
mol = mole
mmol = millimole
mw = molecular weight
TLC = thin layer chromatography
Trt = trityl
AIBN = 2,2'-azobisisobutyronitrile
KtBuO = potassium t-butoxide General Synthesis of the N-α-bromo-4-toluyl-pyrroles
(Schemes 1–4)

Schemes 1 and 2 describe general synthetic pathways to N-4-toluyl-pyrrole derivatives. Treatment of an appropriately substituted 4-amino toluidine 1 with 2,5-diethoxytetrahydrofurane in the presence of a high-boiling protic solvent, gives N-4-toluylpyrroles 2. The reaction is best performed with glacial acetic acid as the solvent and preferably at temperatures between 50° C. and the reflux temperature of the solvent as previously described in the literature [H. Gross, Chem. Ber., 93, 65, (1960); N. Elmin and N. Clauson-Kaas, 6,687, (1952)]. Formylation of the N-4-toluyl-pyrrole is carried out according to the Vilsmeier-Haacks reaction [W. J. Jackson et al., J. Am. Chem. Soc., 103, 533, (1981)]. The reaction is performed with phosphorous oxychloride and dimethylformamide (DMF) with DMF acting as both the reagent and the solvent. The temperature of the reaction may vary between 0° C. and reflux temperature of the DMF. The compounds were generally purified by chromatography on a silica gel column and subsequently recrystallized from a suitable solvent or distilled under reduced pressure. The N-(4-toluyl)-2-formylpyrrole 2 derivatives is then transformed into the desired oxime 3 by treatment with hydroxylamine hydrochloride preferably in a protic solvent such as a lower alcohol in the presence of a base such as the hydroxide or carbonate salt of an alkali, trialkylamine, or sodium hydride and preferably at temperatures between room temperature and 100° C. The oximes 3 isolated by filtration, furnish the 1-(4-toluyl)-2-cyanopyrroles when treated with a dehydration agent. Heating a suspension of the oxime 3 in a carboxylic acid anhydride used as the solvent and the dehydrating agent, at a temperature between 50° C. and 150° C. for a period of time ranging between 1 and 12 hours provides the desired nitrile derivative 4.

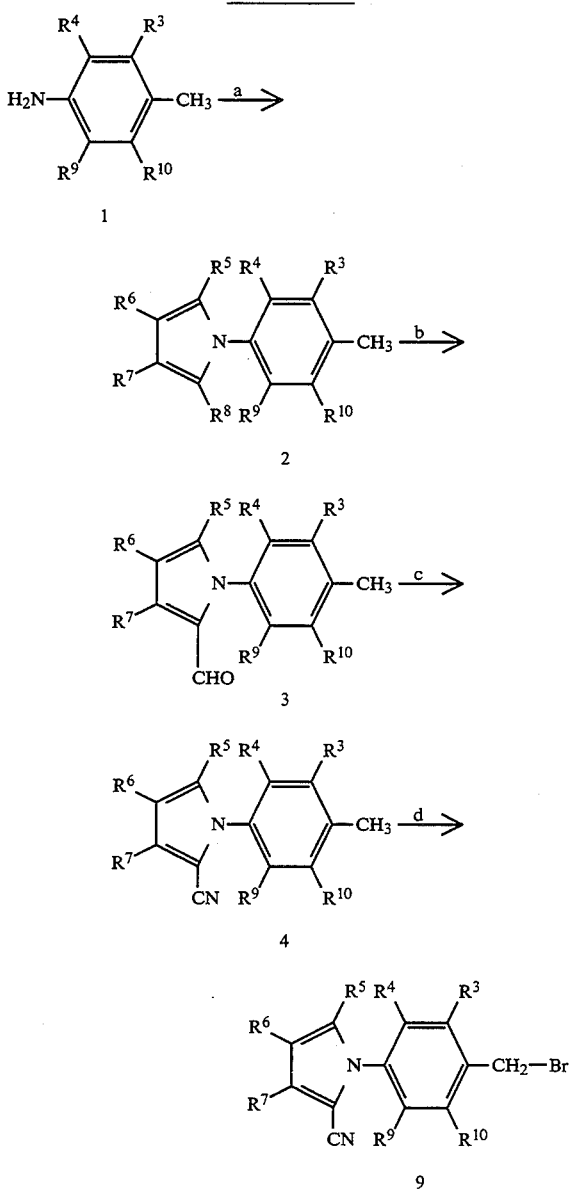

SCHEME 1 wherein the foregoing R substituents are as defined before.
Conditions:

a 2,5-dimethoxytetrahydrofurane; acetic acid reflux 2 h.
b DMF, POCl₃.
c hydroxylamine, methanol; acetic anhydride.
d N-bromosuccinimide, CCl₄, AIBN.

The cyano derivative 4 is reacted by a 1,3-dipolar cycloaddition with trialkyltin azide to produce the corresponding tetrazole 5 as described by K. Sisido et al [*J. Organometal. Chem.*, 33, 337–46 (1971)] (Scheme 2). The reaction is advantageously performed with an excess of the trialkyltin azide in refluxing toluene or dimethylformamide as solvent. The N-(trimethylstannyl)-tetrazole 5 can be converted to the free tetrazole by bubbling anhydrous hydrogen chloride in an ethereal or alcoholic solution, or by treatment with aqueous sodium hydroxide. The unprotected tetrazole intermediate 6 is reacted with an aralkylhalide, such as trityl chloride, which will provide a removable protecting group for the tetrazole. This reaction is best performed with trityl chloride in an inert solvent such as dichloromethane in the presence of at least one equivalent of a non-nucleophilic base such as pyridine or a trialkylamine. The bromination of 7 to give the benzyl bromide 8 is performed with N-bromosuccinimide in the presence of AIBN or dibenzoylperoxide in an inert solvent such as carbon tetrachloride at a temperature from 40° C. to reflux of the solvent used. In most cases, it is advantageous to convert the cyano derivative into the corresponding α-bromotoluyl-2-cyano-pyrrole 9 (Scheme 3). The bromination is performed according to the procedures described above for the conversion of 7 to 8.

SCHEME 2

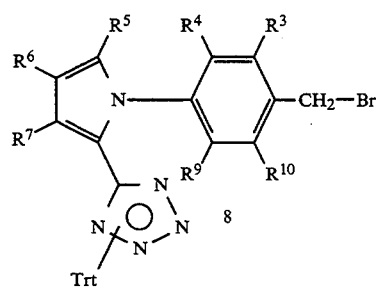

-continued
SCHEME 2

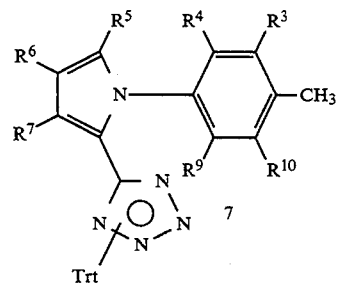

wherein the foregoing R substituents are as defined before.

SCHEME 3

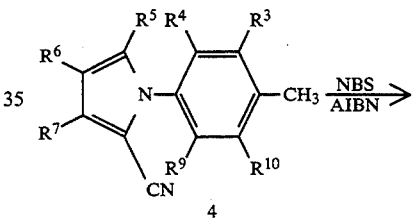

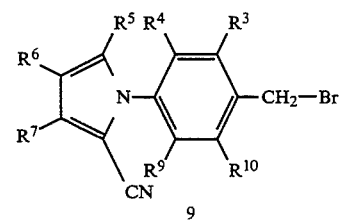

wherein the foregoing R substituents are as defined before.

In some cases, it is advantageous to introduce substituents R⁵-R⁷ on 9. For example, Scheme 4 describes the use of chlorosuccinimide to chlorinate the pyrrole ring to give the dichloro adduct 10.

SCHEME 4

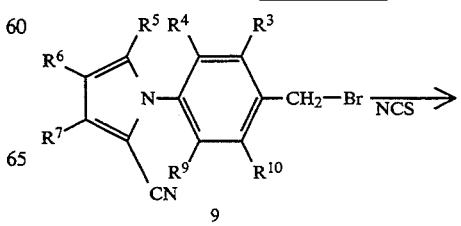

-continued
SCHEME 4

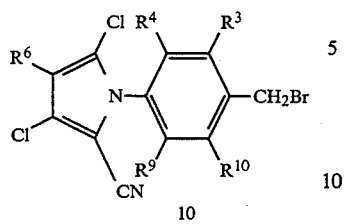

wherein the foregoing R substituents are as defined before.

Preparation of the Imidazoles (Scheme 5)

Schemes 5a–5d describe general synthetic pathways to imidazole derivatives. The imidazole compounds (11) are readily available by any of a number of standard methods. For example, acylaminoketone can be cyclized with ammonia or equivalents thereof [D. Davidson, et al, *J. Org. Chem.*, 2, 319 (1937)] to the corresponding imidazole. The corresponding oxazole can also be converted to imidazole (11) by action of ammonia or amines in general [H. Bredereck, et al, *Ber.*, 88, 1351 (1955); J. W. Cornforth and R. H. Cornforth, *J. Chem Soc.*, 96, (1974)].

Several alternative routes to imidazoles (11) are illustrated in Scheme 5. As shown in Scheme 5a, reaction of the appropriate $R^6$ substituted imidate esters (12) with an appropriately substituted α-hydroxy- or α-haloketone or aldehyde in ammonia leads to imidazoles of formula (11) [P. Dziuron and W. Schunack, *Archiv. Pharmaz.*, 307, 407 (1974)].

The starting imidazole compounds (11) wherein $R^0$ and $R^1$ are both hydrogen can be prepared as shown in equation b) by reaction of the appropriate $R^2$-substituted imidate ester (12) with α-aminoacetaldehyde dimethyl acetal (16) [M. R. Grimmett, *Adv. Heterocyclic Chem.*, 12, 103 (1970)].

As shown in equation 5c, imidazole (13: wherein $R^0$ is hydrogen and $R^1$ is CH2OH) can be prepared by treatment of the imidate ester (12) with 1,3-dihydroxyacetone in ammonia by the procedure described in [*Archive der Pharmazie*, 307, 470 (1974)]. Halogenation of imidazole (13) or any imidazole wherein $R^0$ or $R^1$ is hydrogen is preferably accomplished by reaction with one to two equivalents of N-halosuccinimide in a polar solvent such as dioxane or 2-methoxyethanol at a temperature of 40°–100° C. for 1–10 h.

Imidazoles (11) where $R^0$ and $R^1$ are CN can be prepared as shown in Scheme 5d by reaction or $R^2$ substituted ortho esters, ortho acids or aldehydes (followed by oxidation of the aldehyde) with diamino-maleonitrile (15) by the procedure described by [R. W. Begland et al, *J. Org. Chem.*, 39, 2341 (1974)]. Likewise $R^2$ substituted imidate esters (12) also react with diaminomaleonitrile to give 4,5 dicyanoimidazoles (11).

SCHEME 5

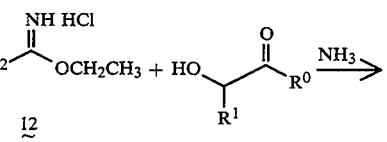

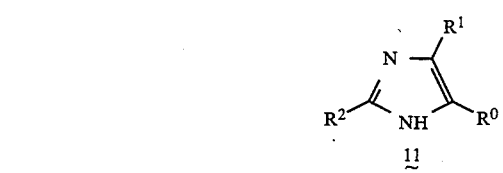

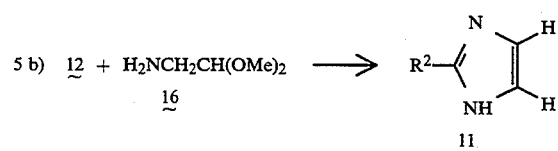

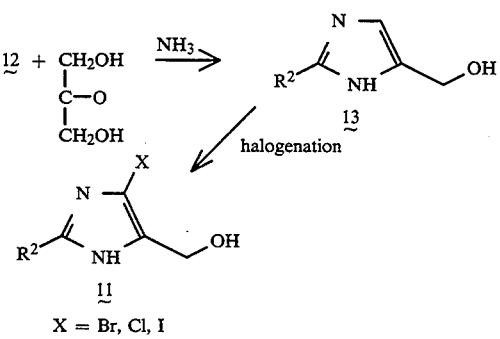

wherein the foregoing R substituents are as defined before.

Alkylation of the Imidazoles (Schemes 6 and 7)

Schemes 6 and 7 show the conversion of imidazoles and N-toluyl-pyrroles intermediates to compound of Formula I carried out by alkylation of the anion of an imidazole 11 with a pyrrole derivative of type 8-10 as the alkylating agent. The leaving group in 8-10 can be an halogen (with the exception of fluorine) group, a tosylate or a mesylate; preferably a bromine atom is the leaving group. The reaction solvent can be methylene chloride, tetrahydrofurane, dioxane, water, dimethylformamide or dimethylsulfoxide and the presence of an acid boiling agent such as sodium, potassium or cesium carbonate, sodium hydroxide, triethylamine, potassium t-butoxide, sodium hydride is required. The most appropriate base is potassium t-butoxide. The reaction is best performed at a temperature between 0° C. and 120° C.

SCHEME 6

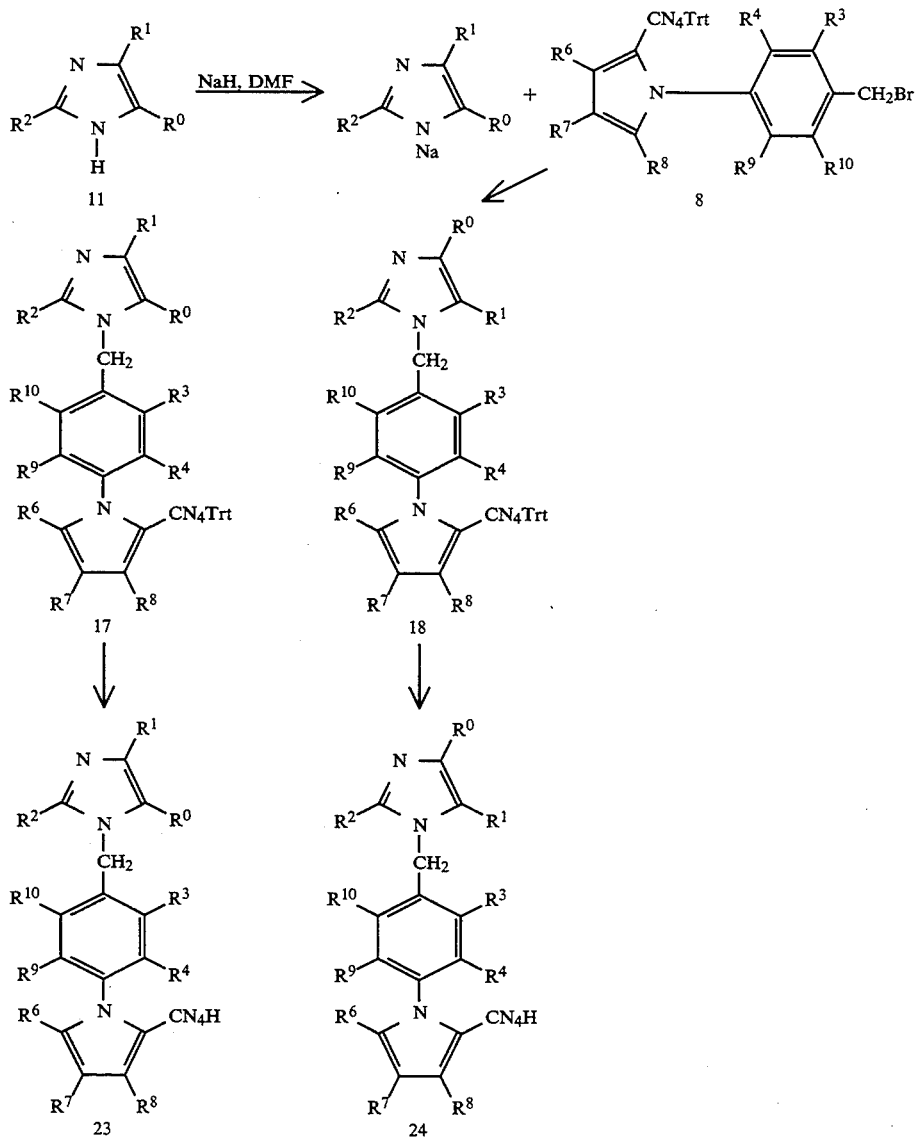

wherein the foregoing R substituents are as defined before.

The anion of 11 when reacted with an alkylating agent 8 gives a mixture of regioisomers 17 and 18. The isomer mixture may be converted to mixtures of the corresponding tetrazoles 23 and 24 by treatment with the appropriate reagent. Or, the isomers 17 and 18 may be separated by chromatographic methods, and each isomer may be reacted with the appropriate reagent to provide the tetrazole-substituted end product. A suitable method as described by Greene in "Protective Group in Organic Synthesis" Wiley-Interscience, 1980, can be used to remove the triphenylmethyl group. Such methods include hydrogenation in the presence of a catalyst such as palladium or platinum and hydrolysis under basic or acidic conditions. The reaction is performed in a solvent or a mixture of solvents such as acetone, water, glacial acetic acid, or a lower alcohol at temperatures preferably between 0° C. and 100° C.

Another route to compounds of Formula I involves the alkylation of an imidazole derivative with a nitrile derivative of type 9 or 10 (Scheme 7). The leaving group in 9 or 10 can be halogen (with the exception of fluorine), tosylate, or mesylate with a bromine being the preferred leaving group. The reaction is best conducted in methylene chloride, acetonitrile, tetrahydrofurane, dioxane, water, dimethylformamide or dimethylsulfoxide in the presence of an acid binding agent such as sodium, potassium or cesium carbonate, sodium hydroxide, triethylamine, potassium t-butoxide or sodium hydride at a temperature between 0° C. and 120° C.

Synthetic Scheme 7 shows the coupling reaction of a imidazole 11 with the appropriate alkylating reagent 9. In the first step, 11 is treated with a base, such as potassium t-butoxide, to generate the corresponding anion. The anion is reacted with the alkylating agent 9 to give a mixture of regioisomers 21 and 22. The isomer mixture may be converted to mixtures of the corresponding tetrazoles 23 and 24 by treatment with the appropriate reagent. Or, the isomers 21 and 22 may be separated by chromatographic methods, and each isomer may be reacted with the appropriate reagent to provide the acid- or tetrazole-substituted end product. The alkylated cyano derivatives (21-22) can be transformed into a compound of Formula I by converting the cyanide group into a tetrazole. Trialkyltin azide (K. Sisido, *J. Organometal Chem.*, 33, 337-66, 1971) is preferably used in a high boiling temperature solvent (Scheme 7). The N(trimethylstannyl) intermediate is converted to the free tetrazole by the action of dilute acid. The tetrazole can also be generated by heating the cyanide derivatives 21 or 22 with sodium azide and ammonium chloride in dimethylformamide at a temperature close to reflux temperature.

mation which is not intended to indicate any conformational preference.

EXAMPLE 1

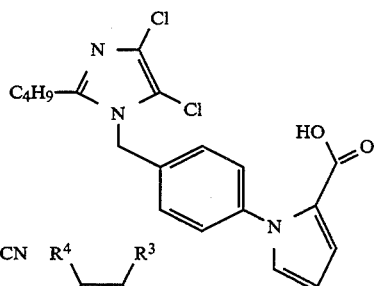

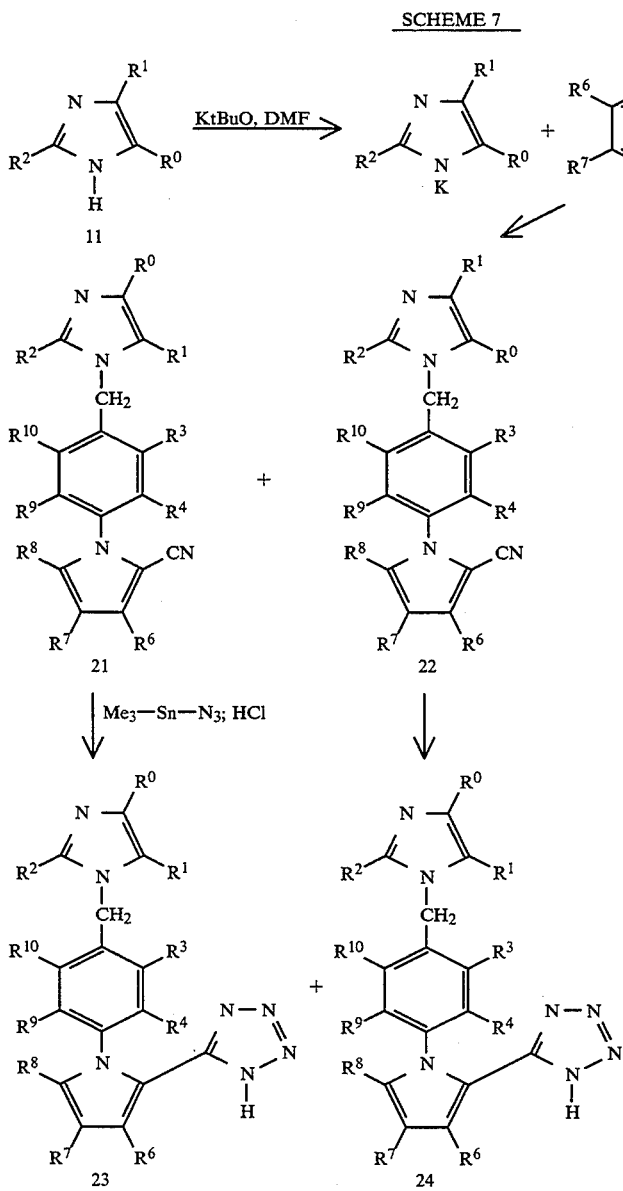

wherein the foregoing R substituents are as defined before.

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees centigrade. The compounds of the examples are graphically represented in an arbitrary confor- 1-[4-[(2-n-butyl-4,5-dichloro-imidazolyl)methyl]-phenyl]-1H-pyrrole-2-carboxylic acid

Step (a): Preparation of 2-formyl-1-(4-methyl)phenyl-1H-pyrrole

In 2 L of acetic acid, were combined 500 g (4.67 mol) of p-toluidine and 625 g (4.73 mol) of 2,5-dimethoxy-3-tetrahydrofurane. The solution was stirred at reflux for 2 h and concentrated to an oil which solidified upon standing. The pyrrole was distilled under vacuum between 110°–155° C. giving 545 g (74%) of the desired material. A solution of 511 g (7 moles) of DMF was cooled in an ice bath and slowly treated with 651 g (7 moles) of phosphorus oxychloride; the mixture was allowed to warm up to 25° C. and stir for 20 min. A solution of the pyrrole in 2.7 L of dry DMF was slowly added. After the addition was complete, the reaction mixture was heated at 110°–120° C. for 3 h, cooled and partitioned between water and ethyl acetate. The organic extract was dried ($Na_2SO_4$) and concentrated in vacuo to give 3.5 moles (100%) of the crude produce as an oil.

Step (b): Preparation of 3-oximino-1-(4-methyl)phenyl-1H-pyrrole

The crude product from Example 1, Step (a) (3.5 moles), was dissolved in 5 L of methanol at reflux. An aqueous solution (2.5 L) of of hydroxylamine hydrochloride 250 g (3.5 moles) and 370 g (3.5 moles) of sodium carbonate was slowly added; the resulting solution was allowed to reflux for an additional 3 h. The reaction mixture was filtered, concentrated under vacuum and partitioned between water and ethyl acetate. The organic extract was dried $Na_2SO_4$ and concentrated to a solid under vacuum.

Step (c): Preparation of 1-(4-methyl)phenyl-1H-pyrrole-2-carbonitrile

The crude oxime (2.5 moles) from Example 1, Step (b) was allowed to reflux in 3 L of acetic anhydride for 3 h. The reaction mixture was concentrated and distilled under vacuum to give 498 g (78% from Step a) of 1-(4-methyl)phenyl-1H-pyrrole-2-carbonitrile as an oil which solidified on standing: mp 56°–58° C.; bp 175°–195° C. (0.5 mm).

Step (d): Preparation of 1-(4-methyl)phenyl-1H-pyrrole-2-carboxylic acid

A 30.6 g sample of the nitrile from Example 1, Step (c) was stirred for 4 h at 167° C. in a mixture of 250 mL of ethylene glycol and 67 g of KOH. The reaction mixture was poured on crushed ice and the pH adjusted to 4 with concentrated hydrochloric acid. A buff colored precipitate was collected which was dried and identified as the acid: mp 182°–4° C.

Step (e): Preparation of 1-(4-methyl)phenyl-1H-pyrrole-2-carboxylic acid, methyl ester The acid from Example 1, Step (d) was dissolved in 100 mL of thionyl chloride. The resulting dark red solution was stirred at 25° C. for 4 h and then concentrated to an oil. Methanol (100 mL) was slowly added and the reaction mixture stirred for 16 h at 25° C. The solution was reconcentrated to an oil and purified by filtration through a pad of silica gel (eluant: methylene chloride). Trituration with hexane gave 22 g of ester: mp 74.2°–74.7° C.; NMR (CDCl$_3$) δ 7.2(m, 4H), 7.05(d, J=7 Hz, 1H), 6.9 (d, J=7 Hz, 1H), 6.25(t, J=7 Hz, 1H), 3.7(s, 3H), 2.4(s, 3H).

Step (f): Preparation of 1-(4-bromomethyl)phenyl-1H-pyrrole-2-carboxylic acid, methyl ester To a mixture of 5.0 g (20 mmol) of the ester from Example 1, Step (e) in 80 mL of carbon tetrachloride was added 3.6 g of N-bromosucinimide followed by 80 mg of AIBN. The reaction was allowed to reflux for 19 h, cooled and filtered to remove the solids; the resulting solution was concentrated an the oil thus produced dissolved in a small amount of ethyl acetate. Trituration with hexane gave 2.5 g of the desired bromo derivative: NMR (CDCl$_3$) δ 7.4(m, 4H), 7.1(d, J=7 Hz, 1H), 6.95(d, J=7 Hz, 1H), 6.25(t, J=7 Hz, 1H), 4.55(s, 2H), 3.75(s, 3H).

Step (g): Preparation of 2-n-butyl-imidazole

An aliquot (100 g) of ethyl iminovalerate [P. Reynaud and R. C. Moreau, Bull. Soc. Chim. France, 2997, (1965)] and 80 g of aminoacetaldehyde diethyl acetal were mixed in a 1000 mL round-bottomed flask. The reaction flask became very warm and a gas was evolved. The reaction mixture was stirred at room temperature for 30 minutes before 70 mL of glacial acetic acid were added, and the heterogeneous mixture stirred at 100° C. for 2.5 h. The reaction mixture was allowed to cool to room temperature and 200 mL of 5N HCl were added. The clear dark brown solution obtained was heated at 100° C. for two more hours before the solution was evaporated to dryness under vacuum. The residue was dissolved in the minimum amount of HCl 5N and the resulting solution extracted with ether. The aqueous phase was made basic by addition of NaOH 2.5% and extracted with dichloromethane. The dichloromethane extracts were pooled, dried over MgSO$_4$ and charcoal and filtered through a pad of cellite. The filtered solution was concentrated in vacuo to provide 60 g (80% yield) of the 2-butyl-imidazole as a reddish oil which solidified on standing (mp 35°–37° C.).

Step (h): Preparation of 2-n-butyl-4,5-dichloro-imidazole

A solution of 5 g of the 2-butyl-imidazole prepared in Example 1, Step (g) in 80 mL of methyl cellosolve and 80 mL dioxane was stirred at room temperature while 6.4 g of N-chlorosuccinimide was added at once. The resulting reaction was stirred for 30 minutes and 3.25 g more of N-chlorosuccinimide were added. After the reaction mixture had stirred for an additional 30 minutes, it was concentrated in vacuo to a volume of approximately 20 mL. Water was added to the residue and the resulting precipitate (3.7 g) collected by filtration and dried (mp 122°–122.8° C.).

Step (i): Preparation of methyl-[4-[(2-n-butyl-4,5-dichloro-imidazolyl)methyl]-phenyl]-1H-pyrrole-2-carboxylate A solution of 321 mg of 2-n-butyl-4,5-dichloro-imidazole (1.7 mmol) in 6 mL dry dimethylformamide was placed in a flask under an atmosphere of nitrogen and 1.7 mL potassium t-butoxide (1N solution in hexane) were added. After stirring the resulting solution at room temperature for 15 minutes, 500 mg of methyl 1-(4-bromomethyl)phenyl-1H-pyrrole-2-carboxylate (1.7 mmol) prepared in Example 1, Step (f), were added at once. The reaction mixture was stirred for 1 h at room temperature and then concentrated in vacuo to an oil which was partitioned between 0.1N NaOH and ethyl acetate. The organic extract, dried on MgSO$_4$ and concentrated in vacuo was chromatographed on 50 g of silica gel with 5% ethyl acetate in chloroforme as eluant to give a colorless solid: NMR (CDCl$_3$) δ 7.3(d, J=6 Hz, 2H), 7.1(m, 3H), 6.9(dd J$_1$=1.5 Hz, J$_2$=2.5 Hz, 1H), 6.29(dd, J$_1$=3 Hz, J$_2$=2.5 Hz, 1H), 5.15(s, 2H), 3.75(s, 3H), 2.6(6, J=7 Hz, 2H), 1.7–1.6(m,2H), 1.432–1.3(m, 2H), 0.95(t, J=7 Hz, 3H).

Step (j): Preparation of [4-[(2-n-butyl-4,5-dichloro-imidazolyl)methyl]phenyl]-1H-pyrrole-2-carboxylic acid A solution of 250 mg of the methyl ester from Example 1, Step (i) in 25 mL of methanol and 25 mL of sodium hydroxide in water (10%) was stirred at ambient temperature overnight. The methanol was removed in vacuo and the pH adjusted to 4 with hydrochloric acid which caused the acid to precipitate. The product was collected by filtration: m.p. 181°–182° C.; MS(FAB) m/e(rel. intensity 392 (60, M+H+), 200(100); HRMS. Calcd for M+H: 392.0933; found: 392.0967.

EXAMPLE 2

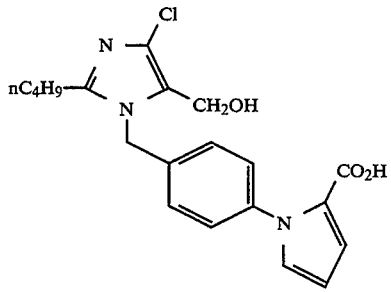

4-[(2-n-butyl-4-chloro-5-hydroxymethyl-imidazolyl)-methyl]phenyl]-1H-pyrrole-2-carboxylic acid Step (a): Preparation of 2-n-butyl-4(5)-hydroxymethyl-imidazole In a steal bomb were added successively 60 g of valeroyl imidate hydrochloride (MW=165, 0.36 mole), 65 g of dihydroxyacetone dimer (MW=180, 0.36 mole) and 400 mL (16 moles) of liquified ammonia. The bomb was stirred and heated at 90° C. for 24 h (pressure increased to about 200 psi). After cooling to 25° C., the ammonia was vented and 1000 mL acetone added to the residue and the precipitate NH$_4$Cl filtered out. The residual solution was quickly filtered through a pad of silica gel using one more liter of acetone to elute the product. After concentration the residual oil was dissolved in 1.2 liter ethyl acetate. A remaining oily residue was decanted and triturated with acetone. Both solutions deposited a crystalline material which was identified as the desired 2-n-butyl-4(5)-hydroxymethyl-imidazole. The dried pale yellow solids combined weighed 32 g (58% yield). The product, which migrates as a single spot on silica gel eluted with 10% MeOH saturated with ammonia in CHCl$_3$ (Rf=0.25), had a melting point of 88.6°–88.8° C. $^1$H NMR (CDCl$_3$, δ ppm): 6.8(s, 1H), 4.6(s,2H), 2.7(t, 2H), 1.7(m, 2H), 1.35(m, 2H), 0.9(t, 3H). FABMS (calc'd for C$_8$H$_{14}$ON$_2$ found): 154.21, 155.

Step (b): Preparation of 2-n-butyl-4(5)-chloro-5(4)-hydroxymethylene imidazole

A solution of 2-n-butyl-5(4)-hydroxymethylene imidazole (40 g, MW 154) in 2 mL of a 1:1 in a mixture of dioxane (490 mL) and 2-methoxyethanol (400 mL) was cooled to −15° C. N-chlorosuccinimide (MW 133.5, 34.7 g) was added and the reaction mixture was stirred at −15° C. for 2 h and allowed to stir 16 h at 25° C. The solvents were removed under vacuum. Water was added to the residue and the solid formed collected by filtration. This solid was then washed twice with water and with methylene chloride before drying (mp: 120°–124° C.): $^1$HNMR (CDCl$_3$, δ ppm): 6.8(s, 1H), 4.6(s, 2H), 2.7(t, 2H), 1.7(m, 2H), 1.35(m, 2H), 1.9(t, 3H). FABMS (calcd for C$_8$H$_{13}$IN$_2$O, found): 280.11, 281.1 (M+H+).

Step (c): Preparation of methyl-[4-[(2-n-butyl-4-chloro-5-hydroxymethyl-imidazolyl)methyl]phenyl]-1H-pyrrole-2-carboxylate A solution of 321 mg of 2-n-butyl-4(5)-chloro-5(4)-hydroxymethylene imidazole (1.7 mmol), from Example 2, Step (b), in 6 mL dry dimethylformamide was placed in a flask under an atmosphere of nitrogen and 1.7 mL potassium t-butoxide (1N solution in hexane) were added. After stirring the resulting solution at room temperature for 15 minutes, 500 mg of methyl 1-(4-bromomethyl)phenyl-1H-pyrrole-2-carboxylate (1.7 mmol) prepared in Example 1, Step (f), were added at once. The reaction mixture was stirred for 1 h at room temperature and then concentrated in vacuo as an oil which was partitioned between 0.1N NaOH and ethyl acetate. The organic extract, dried on MgSO$_4$ and concentrated in vacuo was chromatographed on 50 g of silica gel with 5% ethyl acetate in chloroforme as eluant. The first isomer to elute was the methyl-[4-[2-n-butyl-4-chloro-5-hydroxymethyl-imidazolyl)methyl]-phenyl]-1H-pyrrole-2-carboxylate: NMR (CDCl$_3$) δ 7.3(d, J=6 Hz, 2H), 7.1(m, 3H), 6.9(d, J=2.5 Hz, 1H), 6.25(t, J=3 Hz, 1H), 5.25(s, 2H), 4.45(s, 2H), 3.75(s, 3H), 2.6(t, J=7 Hz, 2H), 1.7–1.6(m, 2H), 1.42–1.3(m, 2H), 0.9(t, J=7 Hz, 3H).

Step (d): Preparation of 4-[(2-n-butyl-4-chloro-5-hydroxymethyl-imidazolyl)-methyl]phenyl]-1H-pyrrole-2-carboxylic acid A solution of 250 mg of the methyl ester from Example 1, Step (i) in 25 mL of methanol and 25 mL of sodium hydroxide in water (10%) was stirred at ambient temperature overnight. The methanol was removed in vacuo and the pH adjusted to 4 with hydrochloric acid which caused the acid to precipitate. The product was collected by filtration: MS(FAB) m/e (rel intensity) 388(90, M+H+, 370(20), 200(100).

EXAMPLE 3 t,700

4-[(2-n-butyl-4-hydroxymethyl-5-chloro-imidazolyl)-methyl]phenyl]-1H-pyrrole-2-carboxylic acid Step (a): Preparation of methyl-[4-[(2-n-butyl-4-hydroxymethyl-5-chloro-imidazolyl)methyl]phenyl]-1H-pyrrole-2-carboxylate A solution of 321 mg of 2-n-butyl-4(5)-chloro-5(4)-hydroxymethylene imidazole (1.7 mmol), from Example 2, Step (b), in 6 mL dry dimethylformamide was placed in a flask under an atmosphere of nitrogen and 1.7 mL potassium t-butoxide (1N solution in hexane)

were added. After stirring the resulting solution at room temperature for 15 minutes, 500 mg of methyl 1-(4-bromomethyl)phenyl-1H-pyrrole-2-carboxylate (1.7 mmol) prepared in Example 1, Step (f), were added at once. The reaction mixture was stirred for 1 h at room temperature and then concentrated in vacuo to an oil which was partitioned between 0.1N NaOH and ethyl acetate. The organic extract dried on MgSO$_4$ and concentrated in vacuo was chromatographed on 50 g of silica gel with 5% ethyl acetate in chloroform as eluant. The first isomer to elute was the methyl-[4-[(2-n-butyl-4-chloro-5-hydroxymethyl-imidazolyl)methyl]phenyl]-1H-pyrrole-2-carboxylate described in Example 2, Step (i). Further solution with ethyl acetate provided the second isomer methyl-[4-[(2-n-butyl-4-hydroxymethyl-5-chloro-imidazolyl)methyl]phenyl]-1H-pyrrole-2-carboxylate: NMR (CDCl$_3$) δ 7.35(d, J=6 Hz, 2H), 7.1(m, 3H), 6.9(d, J=2.5 Hz, 1H), 6.25(t, J=3 Hz, 1H), 5.2(s, 2H), 4.65(s, 2H), 3.75(s, 3H), 2.8(t, J=7 Hz, 2H), 1.8–1.65(m, 2H), 1.43–1.3(m, 2H), 0.9(t, J=7 Hz, 3H).

Step (b): Preparation of 4-[(2-n-butyl-4-hydroxymethyl-5-chloroimidazolyl)methyl]phenyl]-1H-pyrrole-2-carboxylic acid A solution of 250 mg of the methyl ester from Example 3, Step (a) in 25 mL of methanol and 25 mL of sodium hydroxide in water (10%) was stirred at ambient temperature overnight. The methanol was removed in vacuo and the pH adjusted to 4 with hydrochloric acid which caused the acid to precipitate. The product was collected by filtration: mp 180°–181° C.; MS(FAB) m/e (rel. intensity) 388 (80, M+H$^+$), 370(10), 200(100). HRMS. Calcd. for M+H: 388.1428; found: 388.1496.

BIOLOGICAL EVALUATION

Assay A: Angiotensin II Binding Activity

Compounds of the invention were tested for ability to bind to the smooth muscle angiotensin II receptor using a rat uterine membrane preparation. Angiotnesin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co. This assay was carried out according to the method of Douglas et al [*Endocrinology*, 106, 120–124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500× g for 20 min., and the supernatant was recentrifuged at 100,000× g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mM MgCl$_2$, 2 mM EDTA, 0.5% bovine serum albumin, 50 mM Tris-HCl, pH 7.5 and $^{125}$I-AII (approximately 10$^5$ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration (IC$_{50}$) of the tested AII antagonist which gives 50% displacement of the total specifically bound $^{125}$I-II from the high affinity AII receptor. Binding data was analyzed by a nonlinear least-squares curve fitting program. Results are reported in Table I.

Assay B: In Vitro Vascular Smooth Muscle-Response for AII

The compounds of the invention were tested for antagonist activity in rabbit aortic rings. Male New Zealand white rabbits (2–2.5 kg) were sacrificed using an overdose of pentobarbital and exsanguinated via the carotixd arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between movable and fixed ends of a stainless steel wire with the movable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (mM): 130 NaCl, 15 NaHCO$_3$, 15 KCl, 1.2 NaH$_2$PO$_4$, 1.2 MgSO$_4$, 2.5 CaCl$_2$, and 11.4 glucose. The preparations were equilibrated for one hour before approximately one gram of passive tension was placed on the rings. Angiotensin II concentration-response curves were then recorded (3×10$^{-10}$ to 1×10$^{-5}$M). Each concentration of AII was allowed to elicit its maximal contraction, and then AII was washed out repeatedly for 30 minutes before rechallenging with a higher concentration of AII. Aorta rings were exposed to the test antagonist at 10$^{-5}$M for 5 minutes before challenging with AII. Adjacent segments of the same aorta ring were used for all concentration-response curves in the presence or absence of the test antagonist. The effectiveness of the test compound was expressed in terms of pA$_2$ values and were calculated according to H. O. Schild [*Br. J. Pharmacol. Chemother.*, 2, 189–206 (1947)]. The pA$_2$ value is the concentration of the antagonist which increases the EC$_{50}$ value for AII by a factor of 2. Each test antagonist was evaluated in aorta rings from two rabbits. Results are reported in Table I.

Assay C: In Vivo Intraduodenal Pressor Assay Response for AII Antagonists

Male Sprague-Dawley rats weighing 225–300 grams were anesthetized with Inactin (100 mg/kg, i.p.) an catheters were implanted into the trachea, femoral artery, femoral vein and duodenum. Arterial pressure was recorded from the femoral artery catheter on a Gould chart recorder (Gould, Cleveland, Ohio). The femoral vein catheter was used for injections of angiotensin II, mecamylamine and atropine. The tracheal catheter allows for airway patency, and the duodenal catheter was used for intraduodenal (i.d.) administration of test compounds. After surgery, the rats were allowed to equilibrate for 30 minutes. Mecamylamine (3 mg/kg, 0.3 ml/kg) and atropine (400 ug/kg, 0.3 ml/kg) were then given i.v. to produce ganglion blockade. These compounds were administered every 90 minutes throughout the test procedure. Angiotensin II was given in bolus doses i.v. (30 ng/kg in saline with 0.5% bovine serum albumin, 0.1 ml/kg) every 10 minutes three times or until the increase in arterial pressure produced was within 3 mmHg for two consecutive AII injections. The last two AII injections were averaged and were taken as the control AII pressor response. Ten minutes after the final control AII injection, the test compound (dissolved in sodium bicarbonate) was administered i.d. at a dose of 30 mg/kg in a volume of 0.2 ml. Angiotensin II injections were then given 5, 10, 20, 30, 45, 60, 75, 90, and 120 minutes after administration of the test compound and response of arterial pressure was monitored. The response to AII was calculated as percent of the control response and then the percent inhibition is calculated as 100 minus the percent control response. Duration of action of a test compound was defined as the time from peak percent inhibition to 50% of peak. One compound at one dose was tested in each rat. Each test compound was tested in two rats and the values for the two rats were averaged. Results are reported in Table I.

TABLE I

In Vivo and In Vitro Angiotensin II Activity of Compounds of the Invention

| Test Compound Example # | [1]Assay A $IC_{50}$ (μM) | [2]Assay B $pA_2$ | [3]Assay C Inhibition (%) | [3]Assay C Duration (min.) |
|---|---|---|---|---|
| 1 | 5.8 | 5.6 | 74 | 5–10 |
| 2 | 0.87 | 5.8 | 92 | 20–30 |
| 3 | 1.1 | 6.1 | NT | NT |

NT = NOT TESTED
[1]Assay A: Angiotensin II Binding Activity
[2]Assay B: In Vitro Vascular Smooth Muscle Response
[3]Assay C: In Vitro Intraduodenal Pressor Response Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one or ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.01 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.01 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage from containing about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

It is claimed:

1. A therapeutic method for treating a circulatory disorder, said method comprising administering to a subject susceptible to or afflicted with such disorder a therapeutically-effective amount of a compound of Formula I:

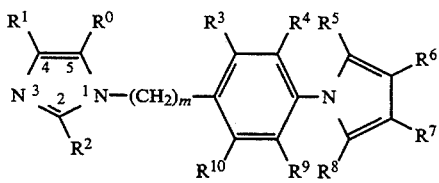 (I)

wherein m is one; wherein each of $R^0$ and $R^1$ is independently selected from methyl, ethyl, n-propyl, isopropyl, n-butyl, sec-butyl, isobutyl, tert-butyl, n-pentyl, isopentyl, neopentyl, phenyl, benzyl, cyclohexyl, cyclohexylmethyl, cyclohexylethyl, n-hexyl, cyclohexanoyl, 1-oxo-2-cyclohexylethyl, benzoyl, 1-oxo-2-phenethyl, 1-oxoethyl, 1-oxopropyl, 1-oxobutyl, 1-oxopentyl, 2-butenyl, 3-butenyl, 2-butynyl, 3-butynyl and 2-hydroxybutyl selected from $CH_3CH_2CH=CH$, $SC_3H_7$, $SC_4H_9$,

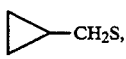

amino, aminomethyl, aminoethyl, aminopropyl, $CH_2OH$, $CH_2OCOCH_3$, $CH_3Cl$, $CH_2OCH_3$, $CH_2OCH(CH_3)_2$, CHO,

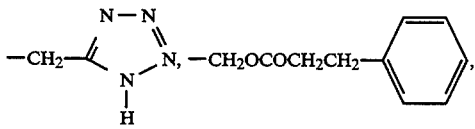

$CH_2CO_2H$, $CH(CH_3)CO_2H$, $NO_2$, $-CONH_2$, $-CONHCH_3$, $CON(CH_3)_2$, $-CH_2-NHCO_2C_2H_5$,

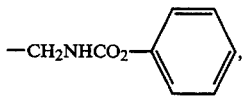

$-CH_2NHCO_2CH_3$, $-CH_2NHCO_2C_3H_7$, $-CH_2NH-CO_2CH_2(CH_3)_2$, $-CH_2NHCO_2C_4H_9$, $CH_2NHCO_2$-adamantyl, $-CH_2NHCO_2$-(1-napthyl), $-CH_2NH-CONHCH_3$, $-CH_2NHCONHC_2H_5$, $-CH_2NH-CONHC_3H_7$, $-CH_2NHCONHC_4H_9$, $-CH_2H-NCONHCH(CH_3)_2$, $-CH_2NHCONH(1-napthyl)$, $-CH_2NHCONH(1-adamantyl)$,

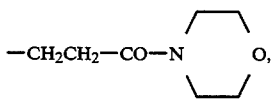

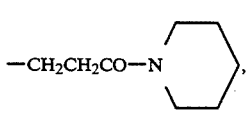

$-CH_2CH_2CH_2CO_2H$, $-CH_2CH_2F$, $-CH_2OCONHCH_3$, $-CH_2OCSNHCH_3$, $-CH_2NH-CSOC_3H_7$, $-CH_2CH_2CH_2F$, $-CH_2ONO_2$,

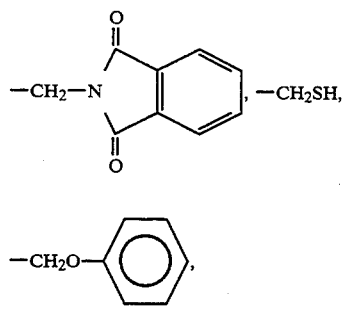

$CF_3$, $CH_2OH$, Br, Cl, F, I, dimethoxymethyl, 1,1-dimethoxypropyl, 1,1-dimethoxypentyl, hydroxyalkyl, 1-oxo-2-phenylethyl, 1-oxo-2-cyclohexylethyl, 1,1-difluoro-2-phenylethyl, monofluoromethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, 2-phenylethyl, 1,1-difluoro-3-phenylpropyl, difluoromethyl, $CO_2H$, $CO_2CH_3$, $CO_2CH_2CH_3$, SH, $PO_3H_2$, $SO_3H$, $CONHNH_2$, $CONHNHSO_2CF_3$, OH,

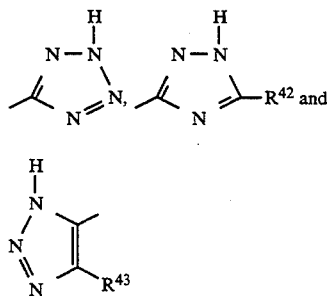

wherein each of $R^{42}$ and $R^{43}$ is independently selected from chloro, cyano, nitro, trifluoromethyl, methoxycarbonyl and trifljuoromethylsulfonyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of $R^3$ through $R^{10}$ is independently selected from hydrido, halo, nitro, trifluoromethyl, hydroxy, alkoxy, cyano, carboxyl, methoxycarbonyl with the proviso that at least one of $R^5$, $R^6$, $R^7$ and $R^8$ is an acidic group selected from $CO_2H$, SH, $PO_3H_2$, $SO_3H$, $CONHNH_2$, $CONHNHSO_2CF_3$, OH,

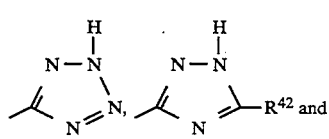

wherein each of $R^{42}$ and $R^{43}$ is independently selected from chloro, cyano, nitro, trifluoromethyl, methoxycarbonyl and trifluoromethylsulfonyl;
or a tautomer thereof or a pharmaceutically-acceptable salt threof.

2. The method of claim 1 wherein m is one; wherein $R^o$ is selected from oxoethyl, 1-oxopropyl, 1-oxobutyl, 1-oxopentyl, 2-butenyl, 3-butenyl, 2-butynyl, 3-butynyl and 2-hydroxybutyl selected from $CH_3CH_2CH=CH$, $SC_3H_7$, $SC_4H_9$,

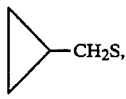

amino, aminomethyl, aminoethyl, aminopropyl, $CH_2OH$, $CH_2OCOCH_3$, $CH_2Cl$, $CH_2OCH_3$, $CH_2OCH(CH_3)_2$, CHO,

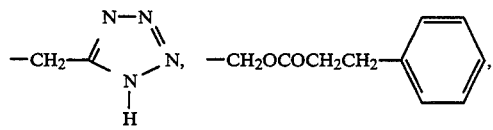

$CH_2CO_2H$, $CH(CH_3)CO_2H$, $NO_2$, $-CO_2CH_3$, $-CONH_2$, $-CONHCH_3$, $CON(CH_3)_2$, $-CH_2-NHCO_2C_2H_5$,

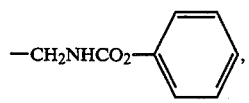

$-CH_2NHCO_2CH_3$, $-CH_2NHCO_2C_3H_7$, $-CH_2NH-CO_2CH_2(CH_3)_2$, $-CH_2NHCO_2C_4H_9$, $CH_2NHCO_2$-adamantyl, $-CH_2NHCO_2$-(1-napthyl), $-CH_2NH-CONHCH_3$, $-CH_2NHCONHC_2H_5$, $-CH_2NH-CONHC_3H_7$, $-CH_2NHCONHC_4H_9$, $-CH_2NH-CONHCH(CH_3)_2$, $-CH_2NHCONH(1$-napthyl), $-CH_2NHCONH(1$-adamantyl),

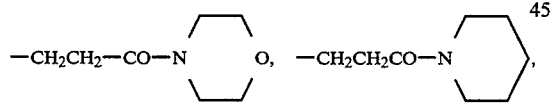

$-CH_2CH_2CH_2CO_2H$, $-CH_2CH_2F$, $-CH_2OCONHCH_3$, $-CH_2OCSNHCH_3$, $-CH_2NHCSOC_3H_7$, $-CH_2CH_2CH_2F$, $-CH_2ONO_2$,

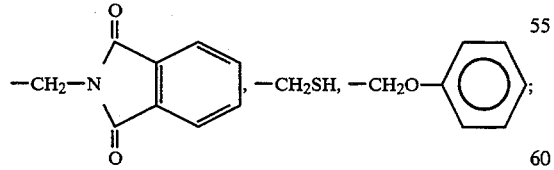

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, $CF_3$, $CH_2OH$, Br, Cl, F, I, dimethoxymethyl, 1,1-dimethoxypropyl, 1,1-dimethoxypentyl, hydroxyalkyl, 1-oxo-2-phenylethyl, 1-oxo-2-cyclohexylethyl, 1,1-difluoro-2-phenylethyl, monofluoromethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, 2-phenylethyl, 1,1-difluoro-3-phenylpropyl, difluoromethyl, $CO_2H$, $CO_2CH_3$, $CO_2CH_2CH_3$, SH, $PO_3H_2$, $PO_3H_2$, $SO_3H$, $CONHNH_2$, $CONHNHSO_2CF_3$ and OH; wherein R2 is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of $R^3$, $R^4$, $R^9$ and $R^{10}$ is hydrido; wherein each of $R^5$ $R^6$, $R^7$ and $R^8$ is independently selected from hydrido, halo, nitro, trifluoromethyl, hydroxy, alkoxy, cyano, carboxyl, methoxycarbonyl with the proviso that at least one of $R^5$ and $R^8$ is an acidic group selected from $CO_2H$ and

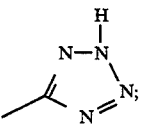

or a tautomer thereof or a pharmaceutically-acceptable salt thereof.

3. The method of claim 2 wherein m is one; wherein $R^0$ is selected from $CH_2OH$, $CO_2H$, CHO, $CO_2CH_3$, $CO_2C_2H_5$, $CH_2OCH_3$, $CH_2OCHOCH_3$ and $CH_2-CO_2C_2H_5$; wherein $R^1$ is selected from Cl, $CF_3$, CHO, n-butyl, cyano, $CO_2CH_3$ and $CO_2CH_2CH_3$; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio and hydroxyalkyl; wherein each of $R^3$, $R^4$, $R^9$ and $R^{10}$ is hydrido; wherein each of $R^5$ $R^6$, $R^7$ and $R^8$ is independently selected from hydrido, halo, nitro, trifluoromethyl, hydroxy, alkoxy, cyano, carboxyl, methoxycarbonyl with the proviso that at least one of $R^5$ and $R^8$ is an acidic group selected from $CO_2H$ and

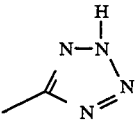

or a tautomer thereof or a pharmaceutically-acceptable salt thereof.

4. The method of claim 3 wherein said compound is selected from compounds and their pharmaceutically-acceptable salts of the group consisting of 1-[4-[(2-butyl-4-chloro-5-hydroxymethyl-1H-imidazol-1-yl)methyl]phenyl]-1H-pyrrole-2-carbonitrile;

1-[4-[(2-butyl-4-chloro-5-hydroxymethyl-1H-imidazol-1-yl)methyl]phenyl]-1H-pyrrole-2-carboxylic acid, methyl, ester;

1-[4-[(2-butyl-4-chloro-5-hydroxymethyl-1H-imidazol-1-yl)methyl]phenyl]-1H-pyrrole-2-carboxylic acid;

5-[1-[4-[(2-butyl-4-chloro-5-hydroxymethyl-1H-imidazol-1-yl)methyl]phenyl]-1H-pyrrol-2-yl]-1H-tetrazole;

5-[1-[4-[(2-butyl-5-chloro-4-hydroxymethyl-1H-imidazol-1-yl)methyl]phenyl]methyl]-1H-pyrrol-2-yl]-1H-tetrazole;

5-[1-[4-[(2-butyl-5-chloro-4-hydroxymethyl-1H-imidazol-1-yl)methyl]phenyl]-3,5-dichloro-1H-pyrrol-2-yl]-1H-tetrazole;

5-[1-[4-[(2-butyl-5-chloro-4-hydroxymethyl-1H-imidazol-1-yl)methyl]phenyl]-1H-pyrrol-3-yl]-1H-tetrazole;

5-[1-[4-[(2-butyl-5-chloro-4-hydroxymethyl-1H-imidazol-1-yl)methyl]phenyl]-5-bromo-1H-pyrrol-2-yl]-1H-tetrazole;

5-[1-[4-[(2-butyl-5-chloro-4-hydroxymethyl-1H-imidazol-1-yl)methyl]phenyl]-5-trifluoromethyl-1H-pyrrol-2-yl]-1H-tetrazole;

5-[1-[4-[(2-butyl-5-chloro-4-hydroxymethyl-1H-imidazol-1-yl)methyl]phenyl]-5-chloro-1H-pyrrol-2-yl]-1H-tetrazole;

5-[1-[4-[(2-butyl-5-chloro-4-hydroxymethyl-1H-imidazol-1-yl)methyl]phenyl]-3-bromo-1H-pyrrol-2-yl]-1H-tetrazole;

5-[1-[4-[(2-butyl-5-chloro-4-hydroxymethyl-1H-imidazol-1-yl)methyl]phenyl]-3,5-dibromo-1H-pyrrol-2-yl]-1H-tetrazole;

5-[1-[4-[(2-butyl-5-chloro-4-hydroxymethyl-1H-imidazol-1-yl)methyl]phenyl]-5-bromo-1H-pyrrol-2-yl]-1H-tetrazole;

1-[4-[(2-butyl-4-hydroxymethyl-5-chloro-1H-imidazol-1-yl)methyl]phenyl]-1H-pyrrol-2-yl-carbonitrile;

1-[4-[(2-butyl-4-hydroxymethyl-5-chloro-1H-imidazol-1-yl)methyl]phenyl]-1H-pyrrol-2-yl-carboxylic acid, methyl, ester;

1-[4-[(2-butyl-4-hydroxymethyl-5-chloro-1H-imidazol-1-yl)methyl]phenyl]-1H-pyrrol-2-yl-carboxylic acid;

5-[1-[4-[(2-butyl-4-hydroxymethyl-5-chloro-1H-imidazol-1-yl)methyl]phenyl]-1H-pyrrol-2-yl]-1H-tetrazole;

5-[1-[4-[(2-butyl-4-hydroxymethyl-5-chloro-1H-imidazol-1-yl)methyl]phenyl]methyl]-1-H-pyrrol-2-yl]-1H-tetrazole;

5-[1-[4-[(2-butyl-4-hydroxymethyl-5-chloro-1H-imidazol-1-yl)methyl]phenyl]-3,5-dichloro-1H-pyrrol-2-yl]-1H-tetrazole;

5-[1-[4-[(2-butyl-4-hydroxymethyl-5-chloro-1H-imidazol-1-yl)methyl]phenyl]-1H-pyrrol-3-yl]-1H-tetrazole;

5-[1-[4-[(2-butyl-4-hydroxymethyl-5-chloro-1H-imidazol-1-yl)methyl]phenyl]-5-bromo-1H-pyrrol-2-yl]-1H-tetrazole;

5-[1-[4-[(2-butyl-4-hydroxymethyl-5-chloro-1H-imidazol-1-yl)methyl]phenyl]-5-trifluoromethyl-1H-pyrrol-2-yl]-1H-tetrazole;

5-[1-[4-[(2-butyl-4-hydroxymethyl-5-chloro-1H-imidazol-1-yl)methyl]phenyl]-5-chloro-1H-pyrrol-2-yl]-1H-tetrazole;

5-[1-[4-[(2-butyl-4-hydroxymethyl-5-chloro-1H-imidazol-1-yl)methyl]phenyl]-3-bromo-1H-pyrrol-2-yl]-1H-tetrazole;

5-[1-[4-[(2-butyl-4-hydroxymethyl-5-chloro-1H-imidazol-1-yl)methyl]phenyl]-3,5-dibromo-1H-pyrrol-2-yl]-1H-tetrazole;

5-[1-[4-[(2-butyl-4-hydroxymethyl-5-chloro-1H-imidazol-1-yl)methyl]phenyl]-5-bromo-1H-pyrrol-2-yl]-1H-tetrazole;

1-[4-[(2-butyl-4,5-dichloro-1H-imidazol-1-yl)methyl]phenyl]-1H-pyrrole-2-carbonitrile;

1-[4-[(2-butyl-4,5-dichloro-1H-imidazol-1-yl)methyl]phenyl]-1H-pyrrole-2-carboxylic acid, methyl ester;

1-[4-[(2-butyl-4,5-dichloro-1H-imidazol-1-yl)methyl]phenyl]-1H-pyrrole-2-carboxylic acid;

5-[1-[4-[(2-butyl-4,5-dichloro-1H-imidazol-1-yl)methyl]phenyl]-1H-pyrrol-2-yl]-1H-tetrazole;

5-[1-[4-[(2-butyl-4,5-dichloro-1H-imidazol-1-yl)methyl]phenyl]methyl]-1H-pyrrol-2-yl]-1H-tetrazole;

5-[1-[4-[(2-butyl-4,5-dichloro-1H-imidazol-1-yl)methyl]phenyl]-3,5-dichloro-1H-pyrrol-2-yl]-1H-tetrazole;

5-[1-[4-[(2-butyl-4,5-dichloro-1H-imidazol-1-yl)methyl]phenyl]-1H-pyrrol-3-yl]-1H-tetrazole;

5-[1-[4-[(2-butyl-4,5-dichloro-1H-imidazol-1-yl)methyl]phenyl]-5-bromo-1H-pyrrol-2-yl]-1H-tetrazole;

5-[1-[4-[(2-butyl-4,5-dichloro-1H-imidazol-1-yl)methyl]phenyl]-5-trifluoromethyl-1H-pyrrol-2-yl]-1H-tetrazole;

5-[1-[4-[(2-butyl-4,5-dichloro-1H-imidazol-1-yl)methyl]phenyl]-5-chloro-1H-pyrrol-2-yl]-1H-tetrazole;

5-[1-[4-[(2-butyl-4,5-dichloro-1H-imidazol-1-yl)methyl]phenyl]-3-bromo-1H-pyrrol-2-yl]-1H-tetrazole;

5-[1-[4-[(2-butyl-4,5-dichloro-1H-imidazol-1-yl)methyl]phenyl]-5-bromo-1H-pyrrol-2-yl]-1H-tetrazole;

1-[4-[(2-butyl-4-pentafluoroethyl-5-hydroxymethyl-1H-imidazol-1-yl)methyl]phenyl]-1H-pyrrol-2-yl-carbonitrile;

1-[4-[(2-butyl-4-pentafluoroethyl-5-hydroxymethyl-1H-imidazol-1-yl)methyl]phenyl]-1H-pyrrol-2-yl-carboxylic acid, methyl ester;

1-[4-[(2-butyl-4-pentafluoroethyl-5-hydroxymethyl-1H-imidazol-1-yl)methyl]phenyl]-1H-pyrrol-2-yl-carboxylic acid;

5-[1-4-[(2-butyl-4-pentafluoroethyl-5-hydroxymethyl-1H-imidazol-1yl)methyl]phenyl]-1H-pyrrol-2-yl]-1H-tetrazole;

5-[1-[4-[(2-butyl-4-pentafluoroethyl-5-hydroxymethyl-1H-imidazol-1-yl)methyl]phenyl]methyl]-1H-pyrrol-2-yl]-1H-tetrazole;

5-[1-[4-[(2-butyl-4-pentafluoroethyl-5-hydroxymethyl-1H-imidazol-1-yl)methyl]phenyl]-3,5-dichloro-1H-pyrrol-2-yl]-1H-tetrazole;

5-[1-[4-[(2-butyl-4-pentafluoroethyl-5-hydroxymethyl-1H-imidazol-1-yl)methyl]phenyl]-1H-pyrrol-3-yl]-1H-tetrazole;

5-[1-[4-[(2-butyl-4-pentafluoroethyl-5-hydroxymethyl-1H-imidazol-1-yl)methyl]phenyl]-5-bromo-1H-pyrrol-2-yl]-1H-tetrazole;

5-[1-[4-[(2-butyl-4-pentafluoroethyl-5-hydroxymethyl-1H-imidazol-1-yl)methyl]phenyl]-5-trifluoromethyl-1H-pyrrol-2-yl]1H-tetrazole;

5-[1-[4-[(2-butyl-4-pentafluoroethyl-5-hydroxymethyl-1H-imidazol-1-yl)methyl]phenyl]-5-chloro-1H-pyrrol-2-yl]-1H-tetrazole;

5-[1-[4-[(2-butyl-4-pentafluoroethyl-5-hydroxymethyl-1H-imidazol-1-yl)methyl]phenyl]-3-bromo-1H-pyrrol-2-yl]-1H-tetrazole;

5-[1-[4-[(2-butyl-4-pentafluoroethyl-5-hydroxymethyl-1H-imidazol-1-yl)methyl]phenyl]-3,5-dibromo-1H-pyrrol-2-yl]-1H-tetrazole;

5-[1-[4-[(2-butyl-4-pentafluoroethyl-5-hydroxymethyl-1H-imidazol-1-yl)methyl]phenyl]-5-bromo-1H-pyrrol-2-yl]-1H-tetrazole;

1-[4-[(2-butyl-4-chloro-5-methoxymethyl-1H-imidazol-1-yl)methyl]phenyl]-1H-pyrrole-2-carbonitrile;

1-[4-[(2-butyl-4-chloro-5-methoxymethyl-1H-imidazol-1-yl)methyl]phenyl]-1H-pyrrole-2-carboxylic acid, methyl ester;

1-[4-[(2-butyl-4-chloro-5-methoxymethyl-1H-imidazol-1-yl)methyl]phenyl]-1H-pyrrole-2-carboxylic acid;

5-[1-[4-[(2-butyl-4-chloro-5-methoxymethyl-1H-imidazol-1-yl)methyl]phenyl]-1H-pyrrol-2-yl]-1H-tetrazole;

5-[1-[4-[(2-butyl-4-chloro-5-methoxymethyl-1H-imidazol-1-yl)methyl]phenyl]methyl]-1H-pyrrol-2-yl]-1H-tetrazole;

5-[1-[4-[(2-butyl-4-chloro-5-methoxymethyl-1H-imidazol-1-yl)methyl]phenyl]-3,5-dichloro-1H-pyrrol-2-yl]-1H-tetrazole;

5-[1-[4-[(2-butyl-4-chloro-5-methoxymethyl-1H-imidazol-1-yl)methyl]phenyl]-1H-pyrrol-3-yl]-1H-tetrazole;

5-[1-[4-[(2-butyl-4-chloro-5-methoxymethyl-1H-imidazol-1-yl)methyl]phenyl]-5-bromo-1H-pyrrol-2-yl]-1H-tetrazole;

5-[1-[4-[(2-butyl-4-chloro-5-methoxymethyl-1H-imidazol-1-yl)methyl]phenyl]-5-trifluoromethyl-1H-pyrrol-2-yl]-1H-tetrazole;

5-[1-[4-[(2-butyl-4-chloro-5-methoxymethyl-1H-imidazol-1-yl)methyl]phenyl]-5-chloro-1H-pyrrol-2-yl]-1H-tetrazole;

5-[1-[4-[(2-butyl-4-chloro-5-methoxymethyl-1H-imidazol-1-yl)methyl]phenyl]-5-bromo-1H-pyrrol-2-yl]-1H-tetrazole;

5-[1-[4-[(2-butyl-4-chloro-5-methoxymethyl-1H-imidazol-1-yl)imidazol-1-yl)methyl]phenyl]-5-bromo-1H-pyrrol-2-yl]-1H-tetrazole;

1-[4-[(2-butyl-4-chloro-5-methoxycarbonyl-1H-imidazol-1-yl)methyl]phenyl]-1H-pyrrol-2-yl-carbonitrile;

1-[4-[(2-butyl-4-chloro-5-methoxycarbonyl-1H-imidazol-1-yl)methyl]phenyl]-1H-pyrrol-2-yl-carboxylic acid, methyl ester;

1-[4-[(2-butyl-4-chloro-5-methoxycarbonyl-1H-imidazol-1-yl)methyl]phenyl]-1H-pyrrol-2-yl-carboxylic acid;

5-[1-4-[(2-butyl-4-chloro-5-methoxycarbonyl-1H-imidazol-1-yl)methyl]phenyl]-1H-pyrrol-2-yl]-1H-tetrazole;

5-[1-[4-[(2-butyl-4-chloro-5-methoxycarbonyl-1H-imidazol-1-yl)methyl]phenyl]methyl]-1H-pyrrol-2-yl]-1H-tetrazole;

5-[1-[4-[(2-butyl-4-chloro-5-methoxycarbonyl-1H-imidazol-1-yl)methyl]phenyl]-3,5-dichloro-1H-pyrrol-2-yl]-1H-tetrazole;

5-[1-[4-[(2-butyl-4-chloro-5-methoxycarbonyl-1H-imidazol-1-yl)methyl]phenyl]-1H-pyrrol-3-yl]-1H-tetrazole;

5-[1-[4-[(2-butyl-4-chloro-5-methoxycarbonyl-1H-imidazol-1-yl)methyl]phenyl]-5-bromo-1H-pyrrol-2-yl]-1H-tetrazole;

5-[1-[4-[(2-butyl-4-chloro-5-methoxycarbonyl-1H-imidazol-1-yl)methyl]phenyl]-5-trifluoromethyl-1H-pyrrol-2-yl]-1H-tetrazole;

5-[1-[4-[(2-butyl-4-chloro-5-methoxycarbonyl-1H-imidazol-1-yl)methyl]phenyl]-5-chloro-1H-pyrrol-2-yl]-1H-tetrazole;

5-[1-[4-[(2-butyl-4-chloro-5-methoxycarbonyl-1H-imidazol-1-yl)methyl]phenyl]-3-bromo-1H-pyrrol-2-yl]-1H-tetrazole;

5-[1-[4-[(2-butyl-4-chloro-5-methoxycarbonyl-1H-imidazol-1-yl)methyl]phenyl]-3,5-dibromo-1H-pyrrol-2-yl]-1H-tetrazole;

5-[1-[4-[(2-butyl-4-chloro-5-methoxycarbonyl-1H-imidazol-1-yl)methyl]phenyl]-5-bromo-1H-pyrrol-2-yl]-1H-tetrazole;

1-[4-[(2-butyl-4,5-dibromo-1H-imidazol-1-yl)methyl]phenyl]-1H-pyrrole-2-carbonitrile;

1-[4-[(2-butyl-4,5-dibromo-1H-imidazol-1-yl)methyl]phenyl]-1H-pyrrole-2-carboxylic acid, methyl ester;

1-[4-[(2-butyl-4,5-dibromo-1H-imidazol-1-yl)methyl]phenyl]-1H-pyrrole-2-carboxylic acid;

5-[1-[4-[(2-butyl-4,5-dibromo-1H-imidazol-1-yl)methyl]phenyl]-1H-pyrrol-2-yl]-1H-tetrazole;

5-[1-[[4-[(2-butyl-4,5-dibromo-1H-imidazol-1-yl)methyl]phenyl]methyl]-1H-pyrrol-2-yl]-1H-tetrazole;

5-[1-[(2-butyl-4,5-dibromo-1H-imidazol-1-yl)methyl]phenyl]-3,5-dichloro-1H-pyrrol-2-yl]-1H-tetrazole;

5-[1-[4-[(2-butyl-4,5-dibromo-1H-imidazol-1-yl)methyl]phenyl]-1H-pyrrol-3-yl]-1H-tetrazole;

5-[1-[4-[(2-butyl-4,5-dibromo-1H-imidazol-1-yl)methyl]phenyl]-5-bromo-1H-pyrrol-2-yl]-1H-tetrazole;

5-[1-[4-[(2-butyl-4,5-dibromo-1H-imidazol-1-yl)methyl]phenyl]-5-trifluoromethyl-1H-pyrrol-2-yl]-1H-tetrazole;

5-[1-[4-[(2-butyl-4,5-dibromo-1H-imidazol-1-yl)methyl]phenyl]-5-chloro-1H-pyrrol-2-yl]-1H-tetrazole;

5-[1-[4-[(2-butyl-4,5-dibromo-1H-imidazol-1-yl)methyl]phenyl]-3-bromo-1H-pyrrol-2-yl]-1H-tetrazole;

5-[1-[4-[(2-butyl-4,5-dibromo-1H-imidazol-1-yl)methyl]phenyl]-5-bromo-1H-pyrrol-2-yl]-1H-tetrazole;

1-[4-[(2-butyl-4-chloro-5-acetoxymethyl-1H-imidazol-1-yl)methyl]phenyl]-1H-pyrrol-2-yl-carbonitrile;

1-[4-[(2-butyl-4-chloro-5-acetoxymethyl-1H-imidazol-1-yl)methyl]phenyl]-1H-pyrrol-2-yl-carboxylic acid, methyl ester;

1-[4-[(2-butyl-5-acetoxymethyl-1H-imidazol-1-yl)methyl]phenyl]-1H-pyrrol-2-yl-carboxylic acid;

5-[1-4-[(2-butyl-4-chloro-5-acetoxymethyl-1H-imidazol-1-yl)methyl]phenyl]-1H-pyrrol-2-yl]-1H-tetrazole;

5-[1-[4-[(2-butyl-4-chloro-5-acetoxymethyl-1H-imidazol-1-yl)methyl]phenyl]methyl]-1H-pyrrol-2-yl]-1H-tetrazole;

5-[1-[4-[(2-butyl-4-chloro-5-acetoxymethyl-1H-imidazol-1-yl)methyl]phenyl]-3,5-dichloro-1H-pyrrol-2-yl]-1H-tetrazole;

5-[1-[4-[(2-butyl-4-chloro-5-acetoxymethyl-1H-imidazol-1-yl)methyl]phenyl]-1H-pyrrol-3-yl]-1H-tetrazole;

5-[1-[4-[(2-butyl-4-chloro-5-acetoxymethyl-1H-imidazol-1-yl)methyl]phenyl]-5-bromo-1H-pyrrol-2-yl]-1H-tetrazole;

5-[1-[4-[(2-butyl-4-chloro-5-acetoxymethyl-1H-imidazol-1-yl)methyl]phenyl]-5-trifluoromethyl-1H-pyrrol-2-yl]-1H-tetrazole;

5-[1-[4-[(2-butyl-4-chloro-5-acetoxymethyl-1H-imidazol-1-yl)methyl]phenyl]-5-chloro-1H-pyrrol-2-yl]-1H-tetrazole;

5-[1-[4-[(2-butyl-4-chloro-5-acetoxymethyl-1H-imidazol-1-yl)methyl]phenyl]-3-bromo-1H-pyrrol-2-yl]-1H-tetrazole;

5-[1-[4-[(2-butyl-4-chloro-5-acetoxymethyl-1H-imidazol-1-yl)methyl]phenyl]-3,5-dibromo-1H-pyrrol-2-yl]-1H-tetrazole; and 5-[1-[4-[(2-butyl-4-chloro-5-acetoxymethyl-1H-imidazol-1-yl)methyl]phenyl]-5-bromo-1H-pyrrol-2-yl]-1H-tetrazole.

5. The method of claim 4 wherein said compound is selected from compounds and their pharmaceutically-acceptable salts of the group consisting of 1-[4-[(2-butyl-4-chloro-5-hydroxymethyl-1H-imidazol-1-yl)methyl]phenyl]-1H-pyrrole-2-carbonitrile;

1-[4-[(2-butyl-4-chloro-5-hydroxymethyl-1H-imidazol-1-yl)methyl]phenyl]-1H-pyrrole-2-carboxylic acid, methyl ester;

1-[4-[(2-butyl-4-chloro-5-hydroxymethyl-1H-imidazol-1-yl)methyl]phenyl]-1H-pyrrole-2-carboxylic acid;

5-[1-[4-[(2-butyl-4-chloro-5-hydroxymethyl-1H-imidazol-1-yl)methyl]phenyl]-1H-pyrrol-2-yl]-1H-tetrazole;

1-[4-[(2-butyl-4-hydroxymethyl-5-chloro-1H-imidazol-1-yl)methyl]phenyl]-1H-pyrrol-2-yl-carbonitrile;

1-[4-[(2-butyl-4-hydroxymethyl-5-chloro-1H-imidazol-1-yl)methyl]phenyl]-1H-pyrrol-2-yl-carboxylic acid, methyl ester;

1-[4-[(2-butyl-4-hydroxymethyl-5-chloro-1H-imidazol-1-yl)methyl]phenyl]-1H-pyrrol-2-yl-carboxylic acid;

5-[1-[4-[(2-butyl-4-hydroxymethyl-5-chloro-1H-imidazol-1-yl)methyl]phenyl]-1H-pyrrol-2-yl]-1H-tetrazole;

1-[4-[(2-butyl-4,5-dichloro-1H-imidazol-1-yl)methyl]phenyl]-1H-pyrrole-2-carbonitrile;

1-[4-[(2-butyl-4,5-dichloro-1H-imidazol-1-yl)methyl]phenyl]-1H-pyrrole-2-carboxylic acid, methyl ester;

1-[4-[(2-butyl-4,5-dichloro-1H-imidazol-1-yl)methyl]phenyl]-1H-pyrrole-2-carboxylic acid;

5-[1-[4-[(2-butyl-4,5-dichloro-1H-imidazol-1-yl)methyl]phenyl]-1H-pyrrol-2-yl]-1H-tetrazole;

1-[4-[(2-butyl-4-pentafluoroethyl-5-hydroxymethyl-1H-imidazol-1-yl)methyl]phenyl]-1H-pyrrol-2-yl-carbonitrile;

1-[4-[(2-butyl-4-pentafluoroethyl-5-hydroxymethyl-1H-imidazol-1-yl)methyl]phenyl]-1H-pyrrol-2-yl-carboxylic acid, methyl ester;

1-[4-[(2-butyl-4-pentafluoroethyl-5-hydroxymethyl-1H-imidazol-1-yl)methyl]phenyl]-1H-pyrrol-2-yl-carboxylic acid;

5-[1-[(2-butyl-4-pentafluoroethyl-5-hydroxymethyl-1H-imidazol-1-yl)methyl]phenyl]-1H-pyrrol-2-yl]-1H-tetrazole;

1-[4-[(2-butyl-4-chloro-5-methoxymethyl-1H-imidazol-1-yl)methyl]phenyl]-1H-pyrrole-2-carbonitrile;

1-[4-[(2-butyl-4-chloro-5-methoxymethyl-1H-imidazol-1-yl)methyl]phenyl]-1H-pyrrole-2-carboxylic acid, methyl ester;

1-[4-[(2-butyl-4-chloro-5-methoxymethyl-1H-imidazol-1-yl)methyl]phenyl]-1H-pyrrole-2-carboxylic acid;

5-[1-[4-[(2-butyl-4-chloro-5-methoxymethyl-1H-imidazol-1-yl)methyl]phenyl]-1H-pyrrol-2-yl]-1H-tetrazole;

1-[4-[(2-butyl-4-chloro-5-methoxycarbonyl-1H-imidazol-1-yl)methyl]phenyl]-1H-pyrrol-2-carbonitrile;

1-[4-[(2-butyl-4-chloro-5-methoxycarbonyl-1H-imidazol-1-yl)methyl]phenyl]-1H-pyrrol-2-carboxylic acid, methyl ester;

1-[4-[(2-butyl-4-chloro-5-methoxycarbonyl-1H-imidazol-1-yl)methyl]phenyl]-1H-pyrrol-2-carboxylic acid;

5-[1-[4-[(2-butyl-4-chloro-5-methoxycarbonyl-1H-imidazol-1-yl)methyl]phenyl]-1H-pyrrol-2-yl]-1H-tetrazole;

1-[4-[(2-butyl-4,5-dibromo-1H-imidazol-1-yl)methyl]phenyl]-1H-pyrrole-2-carbonitrile;

1-[4-[(2-butyl-4,5-dibromo-1H-imidazol-1-yl)methyl]phenyl]-1H-pyrrole-2-carboxylic acid, methyl ester;

1-[4-[(2-butyl-4,5-dibromo-1H-imidazol-1-yl)methyl]phenyl]-1H-pyrrole-2-carboxylic acid;

5-[1-[(2-butyl-4,5-dibromo-1H-imidazol-1-yl)methyl]phenyl]-1H-pyrrol-2-yl]-1H-tetrazole;

1-[4-[(2-butyl-4-chloro-5-acetoxymethyl-1H-imidazol-1-yl)methyl]phenyl]-1H-pyrrol-2-yl-carbonitrile;

1-[4-[(2-butyl-4-chloro-5-acetoxymethyl-1H-imidazol-1-yl)methyl]phenyl]-1H-pyrrol-2-yl-carboxylic acid, methyl ester;

1-[4-[(2-butyl-4-chloro-5-acetoxymethyl-1H-imidazol-1-yl)methyl]phenyl]-1H-pyrrol-2-yl-carboxylic acid; and 5-[1-[4-[(2-butyl-4-chloro-5-acetoxymethyl-1H-imidazol-1-yl)methyl]phenyl]-1H-pyrrol-2-yl]-1H-tetrazole.

6. The method of claim 5 wherein said compound is selected from 1-[4-[(2-butyl-4,5-dichloroimidazolyl)methyl]phenyl]-1H-pyrrole-2-carboxylic acid or a pharmaceutically-acceptable salt thereof.

7. The method of claim 5 wherein said compound is selected from 4-[(2-n-butyl-4-chloro-5-hydroxymethylimidazolyl)methyl]phenyl]-1H-pyrrole-2-carboxylic acid or a pharmaceutically-acceptable salt thereof.

8. The method of claim 5 wherein said compound is selected from 4-[(2-n-butyl-4-hydroxymethyl-5-chloroimidazolyl)methyl]phenyl]-1H-pyrrole-2-carboxylic acid or a pharmaceutically-acceptable salt thereof.

9. The method of claim 1 wherein said circulatory disorder is a cardiovascular disorder.

10. The method of claim 1 wherein said cardiovascular disorder is hypertension.

11. The method of claim 1 wherein said cardiovascular disorder is congestive heart failure.

* * * * *